(12) United States Patent
Fuerst et al.

(10) Patent No.: US 10,499,850 B2
(45) Date of Patent: Dec. 10, 2019

(54) METHODS AND SYSTEMS FOR SCALABLE PERSONALIZED BREATHING FUNCTION

(71) Applicant: Eco-Fusion, Ramat Hasharon (IL)

(72) Inventors: Oren Fuerst, Ramat Hasharon (IL); Alexandre Domingues, Lisbon (PT)

(73) Assignee: Eco-Fusion, Ramat Hasharon (IL)

( * ) Notice: Subject to any disclaimer, the term of this patent is extended or adjusted under 35 U.S.C. 154(b) by 1083 days.

(21) Appl. No.: 14/866,535

(22) Filed: Sep. 25, 2015

(65) Prior Publication Data
US 2018/0220957 A1 Aug. 9, 2018

Related U.S. Application Data

(60) Provisional application No. 62/055,257, filed on Sep. 25, 2014, provisional application No. 62/163,627, filed on May 19, 2015.

(51) Int. Cl.
*A61B 5/02* (2006.01)
*A61B 5/00* (2006.01)
*A61B 5/024* (2006.01)
*A61B 5/16* (2006.01)

(52) U.S. Cl.
CPC ............ *A61B 5/486* (2013.01); *A61B 5/0022* (2013.01); *A61B 5/02405* (2013.01); *A61B 5/165* (2013.01); *A61B 5/742* (2013.01); *A61B 5/6898* (2013.01); *A61B 5/7475* (2013.01)

(58) Field of Classification Search
CPC ..... A61B 5/486; A61B 5/165; A61B 5/02405; A61B 5/0022; A61B 5/742; A61B 5/7475; A61B 5/6998
See application file for complete search history.

(56) References Cited

U.S. PATENT DOCUMENTS

| | | | |
|---|---|---|---|
| 2008/0214903 A1* | 9/2008 | Orbach | A61B 5/486 600/301 |
| 2010/0280338 A1* | 11/2010 | Chou | A61B 5/486 600/301 |
| 2013/0144111 A1* | 6/2013 | Wang | A61M 21/02 600/27 |

* cited by examiner

*Primary Examiner* — Christian Jang
(74) *Attorney, Agent, or Firm* — Greenberg Traurig, LLP

(57) ABSTRACT

In some embodiments, the instant invention provides for a computer-implemented method, including: providing, to a user, in real time, by at least one specialized computing device being specifically programmed with wellbeing management software, at least one personalized breathing instruction via a graphical user interface displayed on the at least one specialized computing device, receiving, in real time, by the at least one specialized programmed computing device, user sensor data from at least one heart rate sensor being associated with the user, determining, in real time, by the at least one specialized programmed computing device, user heart rate variability of the user (user HRV), based, at least in part, on the user sensor data, automatically calculating, by the at least one specialized programmed computing device, a parameter status percentage; providing, to the user, at least one personalized breathing recommendation being configured to modify the parameter status percentage.

7 Claims, 32 Drawing Sheets

METHODS AND SYSTEMS FOR SCALABLE PERSONALIZED BREATHING FUNCTION

RELATED APPLICATIONS

This application claims the priority of U.S. provisional application Ser. No. 62/055,257, entitled "METHOD AND SYSTEM FOR SCALABLE PERSONALIZED BREATHING FUNCTION," filed Sep. 25, 2014; and U.S. provisional application Ser. No. 62/163,627, entitled "METHODS AND SYSTEMS FOR SCALABLE PERSONALIZED BREATHING FUNCTION," filed May 19, 2015, which are incorporated herein by reference in their entireties for all purposes.

FIELD OF THE INVENTION

The embodiments of the present invention relate to systems for providing personalized breathing techniques to a user.

BACKGROUND

Typical biofeedback exercises impose a fixed breathing rate/pattern that the user must follow, independently of his age, gender or physical condition.

SUMMARY OF THE INVENTION

In some embodiments, the instant invention provides for a computer-implemented method, including: providing, to a user, in real time, by at least one specialized computing device being specifically programmed with wellbeing management software, at least one personalized breathing instruction via a graphical user interface displayed on the at least one specialized computing device, where the at least one personalized breathing instruction includes at least: (i) a first indication identifying a first duration for inhaling, and (ii) a second indication identifying a second duration for exhaling; receiving, in real time, by the at least one specialized programmed computing device, user sensor data from at least one heart rate sensor being associated with the user, determining, in real time, by the at least one specialized programmed computing device, user heart rate variability of the user (user HRV), based, at least in part, on the user sensor data, automatically calculating, by the at least one specialized programmed computing device, based on the user HRV, a parameter status percentage, based, at least in part, on a weighted sum of a plurality of user-related parameters, including: (1) a first parameter identifying a Low frequency/High frequency ratio of the user, (2) a second parameter identifying a standard deviation of an instantaneous heart rate signal (SDNN) of the user, (3) a third parameter identifying a heart rate of the user, (4) a fourth parameter identifying a pnn50 of the user, and (5) a fifth parameter identifying a coherence of the user, so as to result in a calculated value of between 0.1-100%; providing, to the user, in real time, by the at least one specialized programmed computing device, based on the parameter status percentage, at least one personalized breathing recommendation being configured to modify the parameter status percentage, where the at least one breathing recommendation includes: (i) a first breathing indication identifying a first adjustment to a breathing rate of the user, (ii) a second breathing indication identifying a second adjustment to a breathing pattern of the user, (iii) or any combination thereof. In some embodiments, the method further includes a third indication identifying a third duration for holding a breath. In some embodiments, the method further includes the plurality of the user-related parameters further including: (6) a root of median squares of differences in successive RR intervals (RMSSD), (7) a power spectrum, (8) a total power, and (9) a deep breathing difference. In some embodiments, the heart rate sensor is resided in one of a mobile phone device associated with the user, a Bluetooth-enabled device, or a heart rate monitor associated with the user. In some embodiments, the heart rate sensor is resided in the at least one specialized programmed computing device. In some embodiments, the at least one specialized programmed computing device is the mobile phone device associated with the user. In some embodiments, the method includes instructing a subject to sufficiently use the method of claim 1, so as to result in a reduction of a blood sugar level of between 10-25%. In some embodiments, the subject is a diabetic patient.

In some embodiments, the instant invention provides for a computer system, including: at least one specialized computing device being specifically programmed with personalized wellbeing management software, where the personalized wellbeing management software is at least configured to: generate at least one personalized breathing instruction including at least: (i) a first indication identifying a first duration for inhaling, and (ii) a second indication identifying a second duration for exhaling; receive, in real time, by the at least one specialized programmed computing device, user sensor data from at least one heart rate sensor being associated with the user, determine, in real time, by the at least one specialized programmed computing device, user heart rate variability of the user (user HRV), based, at least in part, on the user sensor data, automatically calculate, by the at least one specialized programmed computing device, based on the user HRV, a parameter status percentage, based, at least in part, on a weighted sum of plurality of user-related parameters, including: (1) a first parameter identifying a Low frequency/High frequency ratio of the user, (2) a second parameter identifying a standard deviation of an instantaneous heart rate signal (SDNN) of the user, (3) a third parameter identifying a heart rate of the user, (4) a fourth parameter identifying a pnn50 of the user, and (5) a fifth parameter identifying a coherence of the user, so as to result in a calculated value of between 0.1-100%; provide to the user, in real time, by the at least one specialized programmed computing device, based on the parameter status percentage, at least one personalized breathing recommendation being configured to modify the parameter status percentage, where the at least one breathing recommendation includes: (i) a first breathing indication identifying a first adjustment a breathing rate of the user, (ii) a second breathing indication identifying a second adjustment to a breathing pattern of the user, (iii) or any combination thereof. In some embodiments, the system further includes a third indication identifying a third duration for holding a breath. In some embodiments, the system further includes the plurality of the user-related parameters further includes: (6) a root of median squares of differences in successive RR intervals (RMSSD), (7) a power spectrum, (8) a total power, or (9) a deep breathing difference. In some embodiments, the heart rate sensor is resided in one of a mobile phone device associated with the user, a Bluetooth-enabled device, or a heart rate monitor associated with the user. In some embodiments, the heart rate sensor is resided in the at least one specialized programmed computing device. In some embodiments, the at least one specialized programmed computing device is the mobile phone device associated with the user. In some embodiments, the personalized wellbeing management software is further configured to instruct a subject to sufficiently use the method of claim 9, so as to result in a reduction of a blood sugar level of between 10-25%. In some embodiments, the subject is a diabetic patient.

BRIEF DESCRIPTION OF THE DRAWINGS

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

Figure 1:
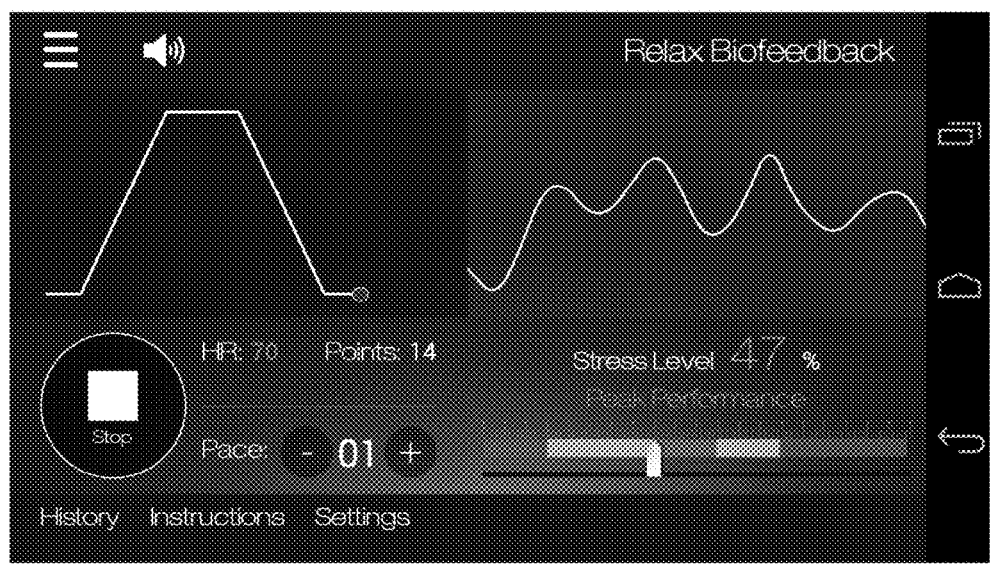
FIG. 1 illustrates an embodiment of the system of the present invention, showing a screenshot that can be displayed on a device. The screenshot shows a display including: an automatically generated breathing guide having an object (e.g., a ball shape) move according to the speed of an exercise, a panel which delivers Heart Rate (HR) and Points according to the received data of the user and exercise conditions, a chart displaying an instantaneous heart rate, and a graphical and numerical indicator of the current stress level.

In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DESCRIPTION OF EXEMPLARY EMBODIMENTS

Among those benefits and improvements that have been disclosed, other objects and advantages of this invention will become apparent from the following description taken in conjunction with the accompanying figures. Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive.

Throughout the description, the following terms take the meanings explicitly associated herein, unless the context clearly dictates otherwise. The phrases "in one embodiment" and "in some embodiments" as used herein do not necessarily refer to the same embodiment(s), though they may. Furthermore, the phrases "in another embodiment" and "in some other embodiments" as used herein do not necessarily refer to a different embodiment, although it may. Thus, as described below, various embodiments of the invention may be readily combined, without departing from the scope or spirit of the invention.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

The present invention will be further explained with reference to the attached drawings, wherein like structures are referred to by like numerals throughout the several views. The drawings shown are not necessarily to scale, with emphasis instead generally being placed upon illustrating the principles of the present invention. Further, some features may be exaggerated to show details of particular components.

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

As used herein, "deep breathing difference" or "DBD" refers to a heart rate change achieved by deep breathing, which can be expressed as the mean of the differences between the maximal and minimal heart rate in, for example, six respiratory cycles.

As used herein, a "respiratory cycle" refers to the events that occur during one breath; i.e., inhalation+exhalation=1 respiratory cycle.

As used herein, the "standard deviation of the normal-to-normal intervals" (SDNN), refers to the square root of variance. Since variance is mathematically equal to total power of spectral analysis, SDNN reflects all the cyclic components responsible for variability in the period of recording. SDNN can be calculated over a 24-hour period and thus encompasses short-term HF variations as well as the lowest-frequency components seen in a 24-hour period.

As used herein, "Heart rate variability" refers to variations of both instantaneous heart rate and RR intervals (i.e. R wave to R wave interval).

As used herein, "instantaneous heart rate" refers to a measurement of the distance between the RR interval on an electrocardiogram (ECG) recording. This value provides the length of one heart beat. The single heart beat then is used to determine the number of heart beats/minute, i.e., instantaneous heart rate.

As used herein, "inter-beat interval" refers to the length of time measured between heart beats.

As used herein, a "parameter" refers to a domain parameter and a frequency parameter.

As used herein, a "Lf/Hf ratio" refers to a parameter derived from the frequency analysis of the instantaneous heart rate signal, where low frequencies range from 0.015-0.15 Hz and high frequencies range from 0.15-0.4 Hz.

As used herein, the "pnn50 parameter" refers to the ratio between the number of instantaneous heart beats with a value equal or higher than 50 ms and the total number of heart beats (i.e., number of instantaneous heart beats with a value equal or higher than 50 ms:total number of heart beats).

As used herein, a device is referred to as being "associated" with a user when the device is positioned at a distance from the user that permits the obtaining and recording of the user's heart rate via the device.

As used herein, "wellbeing" and "wellbeing goals" refer to stress goals, focus goals, and any other goals which typically characterize health.

In some embodiments of the system of the present invention, by monitoring variables extracted from the user's Heart Rate Variability (HRV) and other parameters from the heart rate, in real time, the described system is configured to provide recommendations including adjustments to the breathing rate and/or breathing pattern that will increase the efficiency of the breathing exercise. In some embodiments, once the recommendations are practiced by a user, the breathing exercise becomes personalized and adapted to each individual. The breathing power is the ratio, on the HRV power spectrum, between the power around (±10%) the user's breathing frequency and the total power on the spectrum, where the breathing frequency is determined from the frequency with a higher power in the range of 0.1-0.4 Hz.

In some embodiments, the system is based on the premise that HRV decreases under situations of stress either emotional or physical whereas it increases with rest. HRV may be considered a noninvasive marker of autonomic nervous system function and is used for the diagnosis of diabetic neuropathy. In addition low HRV has prognostic value in patients with myocardial infarction and is associated with risks of cardiac events and sudden deaths. HRV is used for the diagnosis as well as for the prognosis of many diseases. The system utilizes HRV and modifying HRV with a personalized breathing program, whereas the inputs can be recorded using a mobile phone, e.g., by using the mobile camera, by Bluetooth, or a compatible heart rate monitor with a sufficiently high sampling rate.

In some embodiments, relaxation can be achieved by a steady and personalized breathing rate. The steady breathing rate may have a pattern of specific timing to inhale, specific length of time to hold the breath and a specific time to exhale breathing, where a pattern is the relationship between inhaling, exhaling, and stopped breathing, which changes from person to person, and can be dependent on the person's situation (e.g., posture, emotional stress, etc.). The same principle applies to focus, where the breathing pattern of inhale and exhale is intended to increase mental focus. The system includes an algorithm configured to evaluate a person's breathing and selects an efficient manner of breathing to achieve stress reduction (e.g., relaxation) and/or focus enhancement and implements the selected breathing manner during a session, i.e., breathing training. In a non-limiting example, the system includes (1) a biofeedback screen configured to provide breathing training to a user, and (2) a panel configured to show the breathing guide to a user. The screen can further be configured to include a moving color progress ball to show a user when to breath in (e.g., the uphill), when to hold the breath (e.g., the plateau) and when to release (e.g., when the ball is on the slope). The system can further be configured to provide a plurality of images, where the plurality of images can include different types of "cones" which represent different types of breathing patterns. As a non-limiting example, a cone without a plateau reflects a breathing pattern of breathing in and out only (without a hold), and is illustrated in FIG. 1.

The system of the present invention is configured to allow a user to optimize his breathing pattern so as to result in maximizing the exercise efficiency. The optimization is performed by comparing (i) the current breathing guide and (ii) the variation of the instantaneous heart rate during a breathing cycle. If the instantaneous heart rate consistently lags behind the breathing guide, it will slow down. Alternatively, if the instantaneous heart rate consistently tends to oscillate faster (i.e., where the breathing guide thus lags behind the instantaneous heart rate), then the breathing guide will increase its speed. The conscious breathing pattern induces a regulatory effect on the heart rate and simultaneously the user's personal rhythm will induce a feedback control mechanism on the breathing guide. The breathing guide optimization algorithm stabilizes when the breathing guide and instantaneous heart rate are synchronous.

Figure 6:
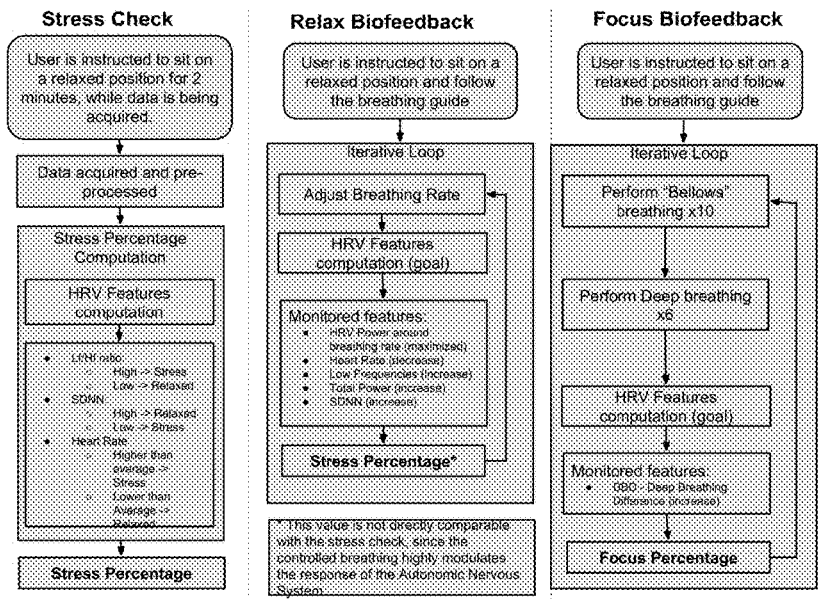
FIGS. 6 and 7 are flow-charts of embodiments of the system of the present invention.
Figure 25:
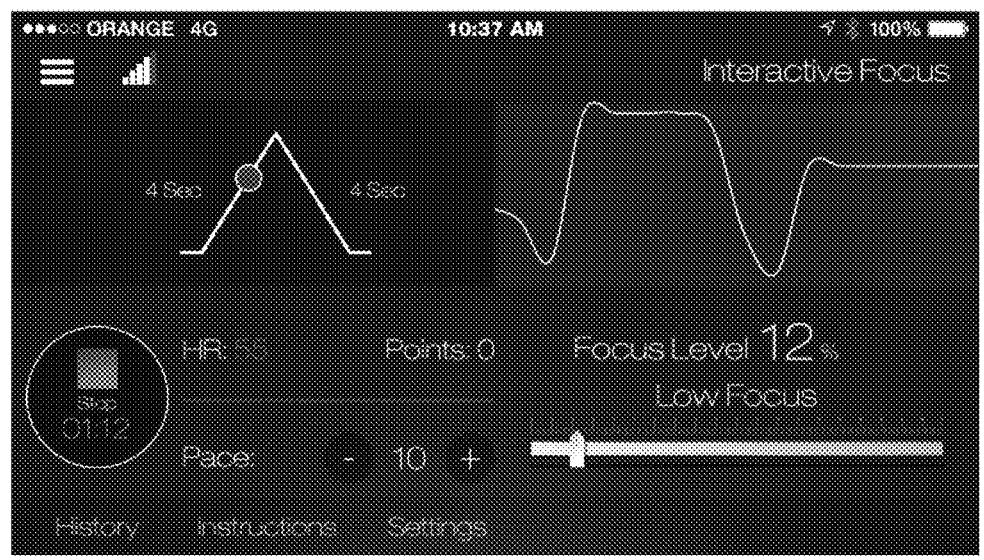
FIGS. 25 and 26A-26C are embodiments of the system of the present invention, showing screenshots that can be displayed on a device.

FIG. 6 is a flow chart illustrating non-limiting exemplary embodiments of the method of the present invention, showing charts directed to: a stress check, relax biofeedback, and focus biofeedback. FIG. 25 shows an image of a subject exhibiting low focus. Additionally, in some embodiments, the present invention can include:

SDNN [ms] Standard deviation of all RR intervals

SDANNi [ms]—Mean value of all standard deviations of all RR intervals for five-minute segments rMSSD [ms]—Root of the median squares of differences in successive RR intervals pNN50 [%] VK [%]—Percentage of successive RR intervals which are >50 ms Standard deviation×100/mean value of all RR intervals In some embodiments, the system of the present invention is configured to include three main data flows, where a data flow can be a general stress check. Under the stress check setting, the user is instructed to sit in a relaxed position for approximately 2 minutes while data is acquired. Data can be acquired via, e.g., a wearable device such as, but not limited to, a Bluetooth connected wristband with heart rate data sampling, or by the user's fingers residing on the phone camera and flash and creating the ability for a PPG sampling (as described herein). The stress percentage computation calculation is performed by calculating the HRV features computation by (1) deriving the Lf/Hf ratio of the user, (2) deriving the standard deviation of successive instantaneous heart rate (SDNN) parameter of the user, and (3) monitoring the user's heart rate. The stress percentage is a function derived from these three parameters by assigning different weights on the parameters, to derive at a stress percentage in the range of 0% to 100%. (e.g., but not limited to, 0.1%, 0.2%, 0.3%, 0.4%, 0.5%, etc.). The stress percentage is a weighted sum between the normalized Heart Rate, normalized Lf/Hf ratio, normalized SDNN, normalized pnn50 and normalized breathing power, where the normalization is a linear regression that projects a calculated value into a 0-100% scale (e.g., but not limited to, 0.1, 0.2, 0.3, 0.4, 0.5, etc.) The Lf/Hf ratio is a parameter derived from the frequency analysis of the instantaneous heart rate signal, where low frequencies range from 0.015-0.15 Hz and high frequencies range from 0.15-0.4 Hz. The pnn50 parameter is the ratio between the number of instantaneous heart beats with a value equal or higher than 50 ms and the total number of heart beats (i.e., number of instantaneous heart beats with a value equal or higher than 50 ms:total number of heart beats).

In some embodiments, under both the relax and focus biofeedback mechanisms, there is an iterative loop that creates a personalized regimen which is built on the premise that when one inhales rapidly, heart rate speeds, and when one exhales, hearts slows. The heart rate can be synced with breathing and HRV can increase as a result of these rapid changes in the heart rates.

Figure 7:
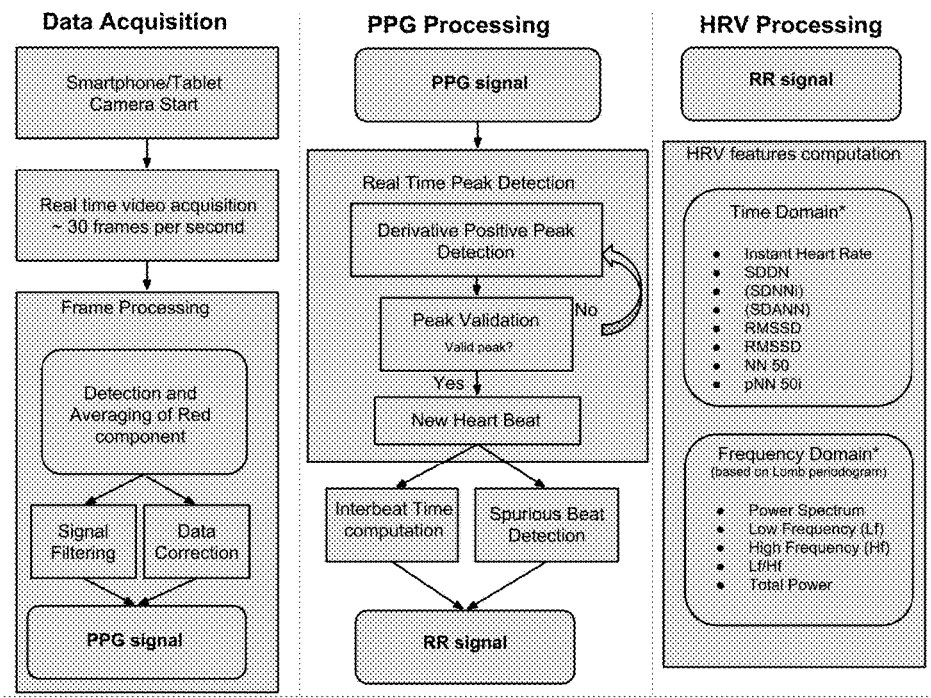

In some embodiments, the stress measurement is iterative, rather than a direct measurement, as a direct measurement is impossible to measure during breathing exercise. The breathing itself disturbs the low frequency HRV signal and artificially spikes the low frequency HRV signal and thus decreases the system's ability to measure stress. In some embodiments, in the relaxation and focus drill, the present invention includes a derivative formula that assesses stress level by evaluating coherence level, inhale/exhale ratio and heartbeat. In some embodiments, stress is not directly extracted from HRV, but inferred, using a formula, from those other indicators. A non-limiting, illustrative example of a method of calculating the inferred stress level is shown in FIG. 7.

In some embodiments, in terms of sampling rates, the camera takes about 30 samples a seconds (varies from phone to phone on android). In some embodiments, the system may use at least one filter, e.g., but not limited to a butterworth filter and/or a band pass filter, to reduce or remove movement and other noise. The system is configured to detect the peaks based on the derivatives of the signal. For example, the system is configured to evaluate at the positive peaks and determines whether the positive peaks are valid. If the positive peaks are valid, the system is configured to determine that the positive peaks are a valid PPG is the variation of the signal. The system is configured to calculate the time differences and filters for deviations of more than 20% from previous samples (e.g., but not limited to, 25%, 30%, 35%, 40%, 45%, etc.).

Figure 26A:
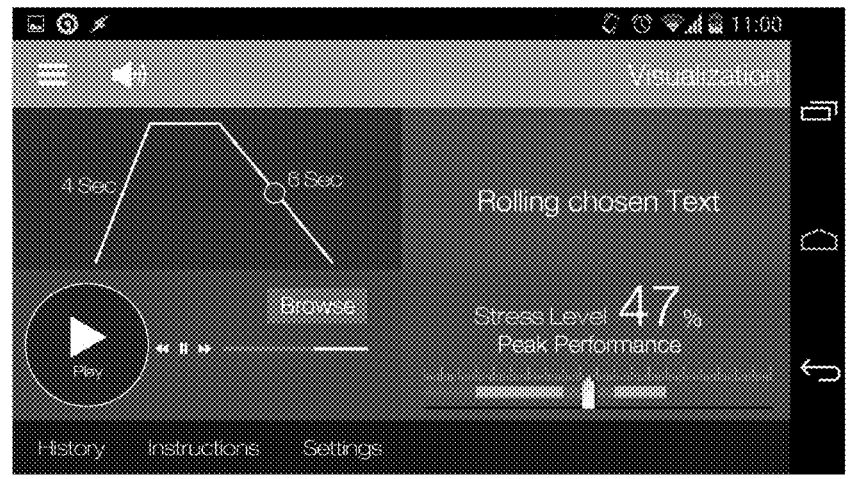
Figure 26B:
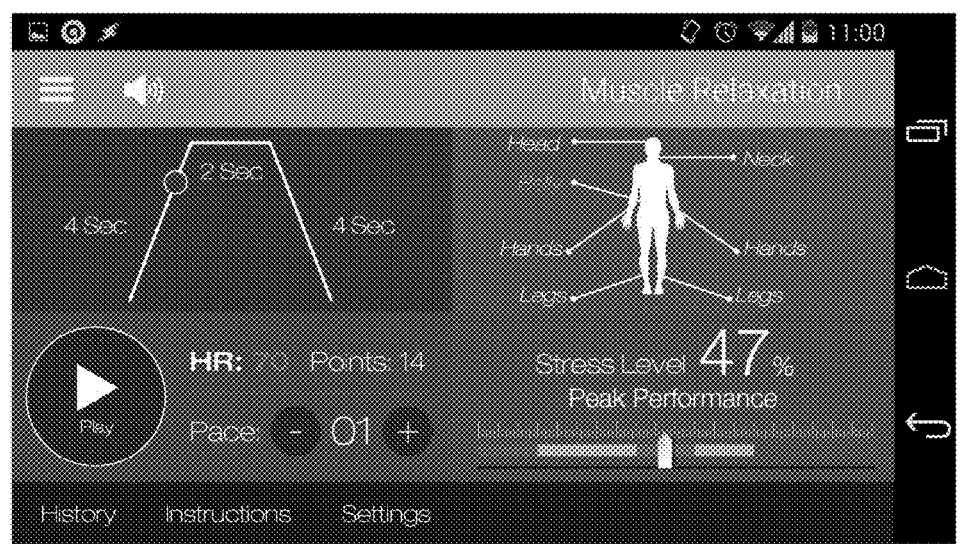
Figure 26C:
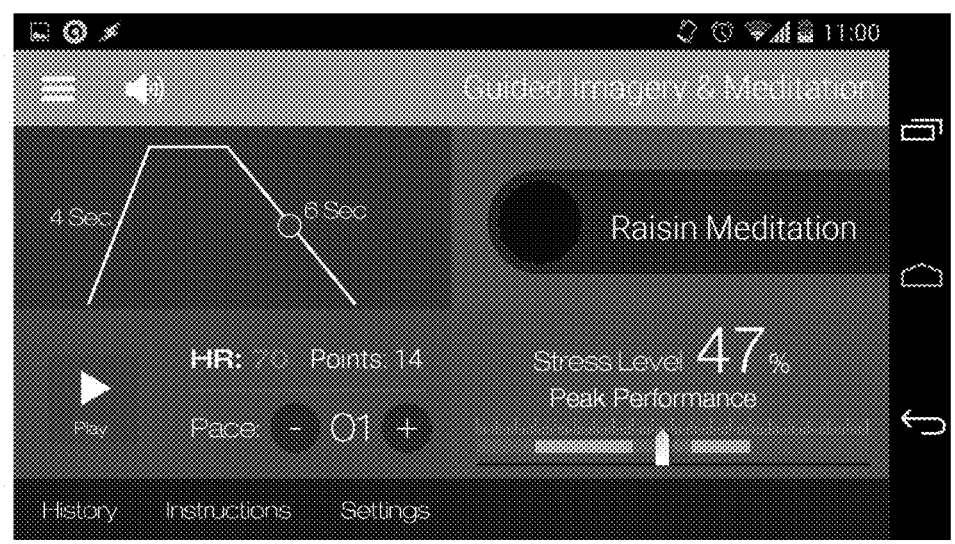

FIGS. 26A-C are screenshots which illustrate breathing drills from cognitive base therapy. In FIG. 26A the breathing exercise is accompanied by calming texts conveyed on the screen and/or calming messages read to a user while conducting the breathing exercise. Conducting both drills together can provide synergistic effect to each of the drills conducted alone. In FIG. 26B, a muscle relaxation drill is accompanying the stress reduction drill. In this drill, the user is instructed to tense his muscles of the body part marked on the screen, and then relax these same muscles. This drill's effectiveness may include the relax Interactive drill. Again, a synergistic effect is expected when the relax interactive drill is combined with the system of the present invention. FIG. 26C shows a screenshot of combining Interactive Relax (or Interactive Focus) technology with guided meditations read to the user. Providing the measurements while conducting the meditation and/or guided imagery drill can increase the effectiveness of these drills.

Illustrative Applications: Sexual Dysfunction

Erectile dysfunction (ED) is defined as the persistent inability to achieve or maintain penile erection sufficient for satisfactory sexual performance. ED is highly prevalent in modern societies, affecting approximately 15% of men under the age of 60 years. In fact, ED is one of the most common chronic medical disorders in men over 40 years of age. It was estimated that in 2005, 25 million men in the United States experienced some degree of ED. ED interferes with multiple aspects of the individual's personal, social, familial and occupational life, leading collectively to chronic stress, psychiatric manifestations (e.g. phobias, depression, obsessions and anxiety) and an impaired quality of life. Congruently, low quality of life, chronic stress and depression can cause chronic activation of the stress system leading to aggravation of ED through several pathogenic pathways, such as chronic latent body inflammation, endothelial dysfunction and metabolic syndrome. As such, effective stress management could reverse the pathogenetic indices of ED, leading to symptom relief. A variety of stress reliefs can be used to relax and alleviate the impact of sexual dysfunction, for example progressive muscle relaxation and visualized breathing.

ED's influence on the quality of life of men can include: sexual performance (hesitation in initiating physical intimacy), relationships with partners (qualitative change in interactions with partners), sexual imaginings (loss of physical or emotional responses to attractive partners), beliefs about masculinity (loss of sexual function diminishing a man's sense of self), changes in sexual function may create adverse emotional outcomes (i.e., anxiety and depression), or any combination thereof. Sexual dysfunction can correlate with anxiety, physiologically inhibiting sexual arousal.

In some embodiments, the method of the present invention includes the interaction of anxiety and cognitive interference. Specifically, in response to a sexual context, low perceived control over one's arousal leads to an attentional shift away from erotic cues and on to one's own physiological arousal and the negative consequences of erectile non-response, thus creating the self-fulfilling feared outcome, namely erectile failure.

Deep and slow breathing (DSB) techniques are widely used in a variety of psychiatric disorders including anxious and depressive syndromes or stress-related disorders. Studies show that combined treatment is more efficacious than phosphodiesterase type 5 inhibitor ("PDE5-I") use alone on sexual satisfaction. However, most people don't know how to utilize DSB properly.

In some embodiments, interactive stress management using the software tool of the present invention can be effective to reduce the symptoms associated with ED (when used with medication or even without) for ED. In particular, the system could be used to increase the efficacy of medications used for daily use, such as, but not limited to, Cialis, and could be used with medication used prior for sexual intercourse such as Viagra, Levitra, Cialis, Staxyn, Muse, or their generic variants based on Sildenafil, tadalafil, vardenafil etc.

In some embodiments, the method of the present invention includes implementing the method at the time of taking the ED pill. If more than an hour has passed between the time of taking the pill and sex, the user could use the application again before attempting sex.

In some embodiments, when a subject diagnosed with ED uses the inventive method, the subject's symptoms of ED are reduced, e.g., but not limited to, 1%, 5%, 10%, 15%, etc.

Illustrative Applications: Anxiety and Panic Disorder

A panic disorder is an anxiety disorder characterized by recurring panic attacks, causing a series of intense episodes of extreme anxiety during panic attacks. It may also include significant behavioral changes lasting at least a month and of ongoing worry about the implications or concern about having other attacks. The latter are called anticipatory attacks (DSM-IVR).

Panic disorder is not the same as agoraphobia (fear of public places), although many afflicted with panic disorder also suffer from agoraphobia. Panic attacks cannot be predicted, and, therefore an individual may become stressed, anxious or worried wondering when the next panic attack will occur. Panic disorder may be differentiated as a medical condition, or chemical imbalance. The DSM-IV-TR describes panic disorder and anxiety differently. Whereas anxiety is preceded by chronic stressors which build to reactions of moderate intensity that can last for days, weeks or months, panic attacks are acute events triggered by a sudden, out-of-the-blue cause: duration is short and symptoms are more intense. Panic attacks can occur in children, as well as adults.

Typical treatment guidelines American Psychiatric Association and the American Medical Association primarily recommend either cognitive-behavioral therapy or one of a variety of psychopharmacological interventions. Some evidence exists supporting the superiority of combined treatment approaches.

Another option is self-help based on principles of cognitive-behavioral therapy. Using a book or a website, a person does the kinds of exercises that would be used in therapy, but they do it on their own, perhaps with some email or phone support from a therapist.

The software can be useful in preventing the prevalence and reducing the severity of the illness. In addition to the use of the software that could be used on a daily basis, one could add daily questionnaires to ask about the lead indicating symptoms (such as morning dryness of the mouth). Changes in the answers will trigger a course of action by the software such as a message to a coach, doctor or a family member, as well as to additional drills, such as a longer relaxation drill. The cognitive behavioral treatment options can be combined to provide an additional treatment. For example, the illustration shows a combination of visualization and interactive relaxation by combining calming messages communicated on the screen with the interactive breathing exercise. Similarly, recorded guided meditation can be combined with the interactive relaxation breathing exercise. Similarly, progressive muscle relaxation (e.g., where rotating body parts are instructed to be tensed and relaxed) could be mixed with the personalized breathing interactive relax drill described wherein. Similar combinations can be used for addressing anxiety, depression and other mental health indications where cognitive behavioral therapy and breathing exercise can be beneficial.

In some embodiments, when a subject diagnosed with anxiety and panic disorder uses the inventive method, the subject's symptoms of anxiety and panic disorder are reduced, e.g., but not limited to, 1%, 5%, 10%, 15%, etc.

Illustrative Application: Attention Deficit Hyperactivity Disorder

In some embodiments, deep breathing can be used to reduce symptoms associated with Attention Deficit Hyperactivity Disorder (ADHD). Interactive breathing has the advantage of providing accurate measurement as to the effectiveness of the guided breathing and the accuracy of its conduct. The system of the present invention could be used for relaxation and/or focus. One method of using it with ADHD patients is to have them use the interactive FOCUS breathing drills in the mornings, when they suffer mainly from focus problems, and the interactive RELAXATION drill in the afternoon, when the effect of their ADHD medication fades and side effects of the medication are prevalent.

In some embodiments, a population of people who take short acting methylphenidate or amphetamine experience irritability or depression for an hour as the stimulant wears off. Sometimes this is worse than the individual's behavior before the medication was started. The present system can be used for the subject patients when the stimulant is wearing off.

In some embodiments, when a subject diagnosed with ADHD uses the inventive method, the subject's symptoms of ADHD are reduced, e.g., but not limited to, 1%, 5%, 10%, 15%, etc.

Illustrative Application: Diabetes

Stress is a physical and mental reaction to perceived danger. Conditions that seen uncontrollable or require emotional and behavioral change tend to be perceived as a threat. When the body and mind sense a threat, they get ready to either run or fight. Whether the threat is real or imagined, the body prepares for survival by turning up some bodily functions while turning others down. In either case, over time these changes are serious and over time are harmful. Excessive stress works against diabetes management by: increasing blood glucose levels (quickly and substantially); inciting strong negative emotions; impairing sound thinking and decision-making; tempting compulsive, poor eating, or any combination thereof. Whether or not a person has diabetes, over time, stress is harmful because it causes so much wear and tear on the body. For example, the heart works faster and harder in preparation for physical action. The increase in pulse and blood pressure causes a strain on the heart, veins and arteries.

In some embodiments, mammals (e.g., but not limited to, humans) under physical or mental stress have elevated glucose levels. In some embodiments, a person's glucose levels go up with mental stress. In some embodiments, a person's glucose level can go down with reduced mental stress. In people with type 2 diabetes, mental stress often raises blood glucose levels. Physical stress, such as illness or injury, can cause higher blood glucose levels in people with either type of diabetes. Interactive Relaxation drills can be used by people with diabetes in order to stabilize and reduce their glucose levels.

As an example, the following are the results of a clinical study conducted with diabetes patients (with A1C above 7%) who were prescribed to conduct the personalized interactive relaxation drills described herein three times a day, along with a healthy diet (which they were educated about before the study as well but did not adhere to). The sugar levels (as measured by A1C) after less than 3 months dropped by an average of 1.75 (18.5%) (see table for data per patient). The results were at significance level of 99%.

| in % | change | post A1c | pre A1c | |
|---|---|---|---|---|
| −17.11% | −1.3 | 6.3 | 7.6 | 1 |
| −46.39% | −4.5 | 5.2 | 9.7 | 2 |
| −9.89% | −0.9 | 8.2 | 9.1 | 3 |
| −41.35% | −4.3 | 6.1 | 10.4 | 4 |
| 8.51% | 0.8 | 10.2 | 9.4 | 5 |
| −10.87% | −1 | 8.2 | 9.2 | 6 |
| −12.50% | −1.1 | 7.7 | 8.8 | 7 |
| −18.51% | −1.757142857 | 7.414285714 | 9.171428571 | average |
| −12.50% | 1.935507808 | | | Standard Deviation |
| 3.9185 | −2.40193452 | | | z |
| 0.994737658 | 0.991845686 | | | Significance Level |

In some embodiments, when a subject diagnosed with diabetes uses the inventive method, the subject's symptoms of diabetes (e.g., but not limited to, glucose level) are reduced, e.g., but not limited to, 1%, 5%, 10%, 15%, etc.

Illustration Application: Insomnia and Sleep Quality

Insomnia is a typical symptom of stress that responds to daily breathing exercise practice in the form of improved sleep quality. As a result, the described interactive and techniques can be used to treat insomnia. Furthermore, relaxation techniques typically increase the percentage of time during sleep when a patient is in REM (rapid eye movement, the stage of sleep most associates with dreaming) phase, a phase that is linked to creativity in the ensuing day. Additionally, a night following cyclic meditation (CM), the percentage of slow-wave sleep (SWS) is higher than in the night following supine rest (SR), whereas the percentage of REM sleep and the number of awakenings per hour were less. For example, in a study of cancer survivors suffering from sleep disturbances, 410 survivors were accrued (96% female; mean age, 54 years; 75% had breast cancer). Half of the survivors were trained with Yoga for Cancer Survivors program consisting of pranayama (breathing exercises), 16 Gentle Hatha and Restorative yoga asanas (postures), and meditation. Participants attended two 75-minute sessions per week. Participants demonstrated greater improvements in global sleep quality and, secondarily, subjective sleep quality, daytime dysfunction, wake after sleep onset, sleep efficiency, and medication use at post-intervention (all $P \leq 0.05$) compared with standard care participants.

The system of the present invention includes a method of breathing that is personalized and providing a high efficacy level of relaxation, thereby increasing the REM portion during the sleep, and enhancing sleep quality (as measured by number of times of awaking).

In some embodiments, when a subject diagnosed with insomnia uses the inventive method, the subject's symptoms of insomnia are reduced, e.g., but not limited to, 1%, 5%, 10%, 15%, etc.

Illustration Application: Irritable Bowel Syndrome

Stress is a major driver in IBS, and stress reduction techniques using breathing could alleviate the IBS symptoms.

For example, a study was performed where a conventional group (n=12, 1 dropout) was given symptomatic treatment with loperamide 2-6 mg/day for two months, and the yogic intervention group (n=9) consisted of a set of 12 asanas (e.g., yogic poses, i.e., Vajrasana, Shashankasana, Ushtrasana, Marjariasana, Padhastasana, Dhanurasana, Trikonasana in two variations, Pawanmuktasana, and Paschimottanasana) along with Surya Nadi pranayama (right-nostril breathing) two times a day for two months. Two months of both conventional and yogic intervention showed a significant decrease of bowel symptoms and state anxiety. This was accompanied by an increase in electrophysiologically recorded gastric activity in the conventional intervention group and enhanced parasympathetic reactivity, as measured by heart rate parameters, in yogic intervention group.

In some embodiments, a user's following the inventive methods can alleviate the IBS symptoms in a high degree.

In some embodiments, when a subject diagnosed with IBD uses the inventive method, the subject's symptoms of IBD are reduced, e.g., but not limited to, 1%, 5%, 10%, 15%, etc.

Illustration Application: Migraines

Personalized interactive relaxation can be used to alleviate the frequency and severity of migraines as well as to reduce the level of medication. For example, seventy-two patients with migraines without aura were randomly assigned to yoga therapy (which included, e.g., deep breathing drills aside from a set of yogic postures) or self-care group for three months. Primary outcomes were headache frequency (e.g., as memorialized by a headache diary), severity of migraine (e.g., as measured by a 0-10 numerical scale) and pain component (e.g., as assessed using a McGill pain questionnaire). Secondary outcomes were anxiety and depression (e.g., as measured using a Hospital anxiety depression scale), and medication score. After adjustment for baseline values, the subjects' complaints related to headache intensity (P<0.001), frequency (P<0.001), pain rating index (P<0.001), affective pain rating index (P<0.001), total pain rating index (P<0.001), anxiety and depression scores (P<0.001), symptomatic medication use (P<0.001) were significantly lower in the yoga group compared to the self-care group.

In some embodiments, when a subject diagnosed with migraines uses the inventive method, the subject's symptoms of migraines are reduced, e.g., but not limited to, 1%, 5%, 10%, 15%, etc.

Illustration to PTSD

Tsunami refugees showed dramatic improvement in post-traumatic stress disorder (PTSD) and depression scores after SKY training. In some embodiments, interventions can be used which include interactive relax breathing which has components similar to yoga, viz. SKY and MCYI can be used, providing personalization and measures of breathing effectiveness on reducing trauma driven stress.

In some embodiments, when a subject diagnosed with PTSD uses the inventive method, the subject's symptoms of PTSD are reduced, e.g., but not limited to, 1%, 5%, 10%, 15%, etc.

Illustration for Melancholic Depression

The stress reduction techniques can be used to assist in treating mild and severe depression. In some embodiments, electroconvulsive therapy (ECT), imipramine, or SKY can be used with the method of the present invention. In some embodiments, SKY and interactive relaxation can be used to treat mild and melancholic depression in dysthymic and unipolar major depressives. Depressed people have a particular EEG brainwave abnormality, which is measured by P300 event related potential (ERP) amplitude. By day 30, there is significant relief from depression in the groups treated with SKY, as measured by the P300 amplitude and standard depression scales. By day 90, P300 amplitude can return to normal and allow each patient to be stable and depression free, or at least significantly reduced symptoms of instability and/or depression. Personalized interactive relaxation technique operates on similar mechanisms while providing immediate feedback re the effectiveness of the breathing exercise and the providing of personalized regimen.

In some embodiments, when a subject diagnosed with depression uses the inventive method, the subject's symptoms of depression are reduced, e.g., but not limited to, 1%, 5%, 10%, 15%, etc.

Illustration for Alcohol and Tobacco Addiction

Stress is typically linked to the habit of tobacco and alcohol consumption, which in turn leads to disease states. Stress Reduction technique using the methodology described above can be used in order to assist in smoking cessation programs. For example, SKY (a breathing technique) can help to control the tobacco habit in 21% of individuals who were followed up to 6 months of practice. A personalized breathing exercise using the methodology illustrated herein can be used to provide immediate feedback as to the effectiveness of the breathing in reducing the stress level of the patient and the rendering of an effective and dynamic personalized regimen.

In some embodiments, when a subject diagnosed with addiction uses the inventive method, the subject's symptoms of addiction are reduced, e.g., but not limited to, 1%, 5%, 10%, 15%, etc.

Description of Calculating Stress Level when Using Breathing Exercise

In some embodiments, the process begins by placing the finger on the camera and flash and following the instructions (inhaling when the ball is on the left axis, hold breathing when it is on the plateau and exhale on the right side). In some embodiments, the square in the middle is highlighting what is seen by the camera and the red is in fact what the camera sees, which is the illuminated finger skin.

Figure 8A:
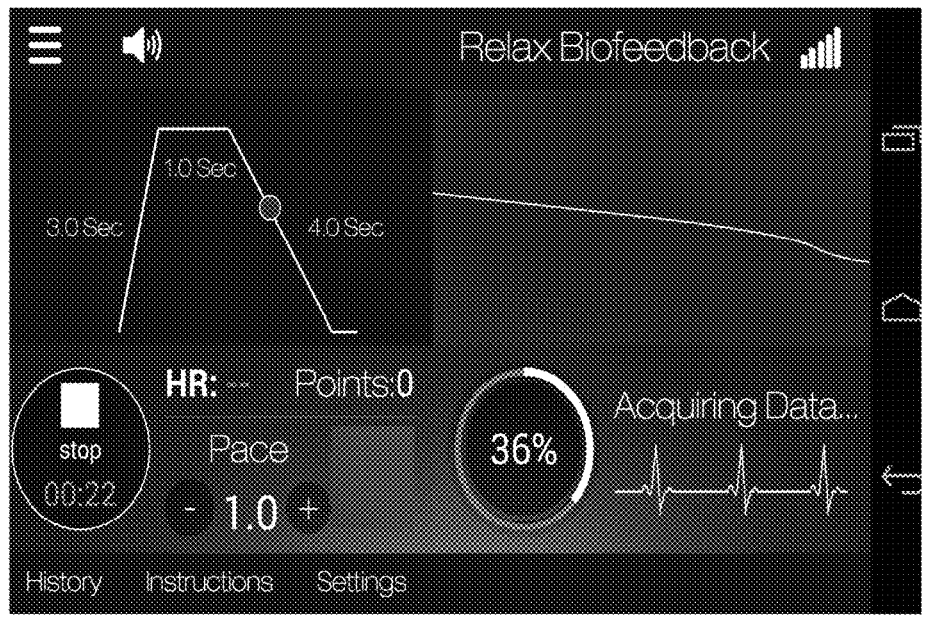
FIGS. 8A-8B, 9, and 10A-10C are embodiments of the system of the present invention, showing screenshots that can be displayed on a device.
Figure 8B:
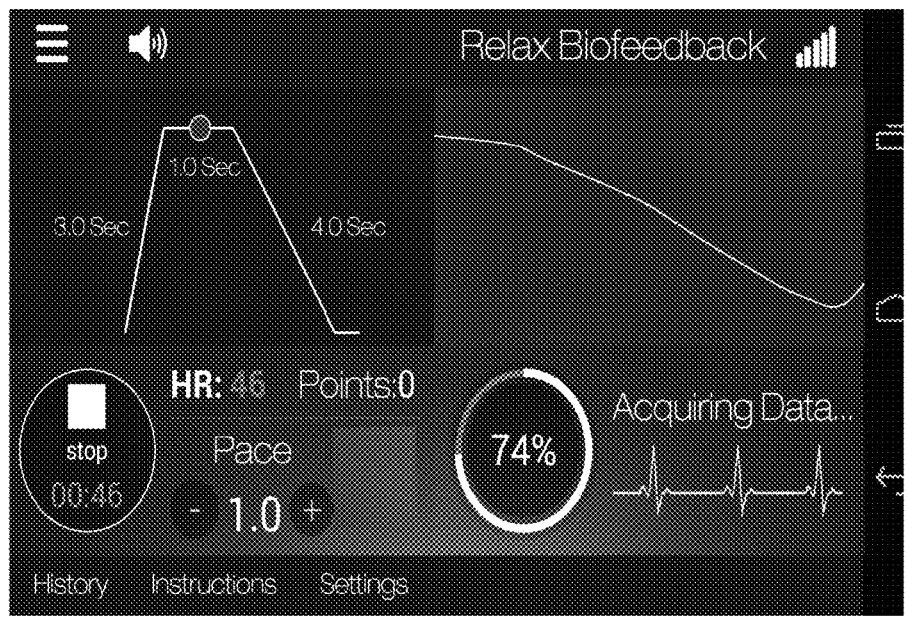

In some embodiments, there is a progress indication (below 36% and on the following screen 74%) shows how much data was acquired thus far in order to provide the initial stress level indication. In some embodiments, with regular phones, it typically takes between 30 seconds to 1 minute. FIGS. 8A and 8B show examples of the use of the method of the present invention.

Figure 9:
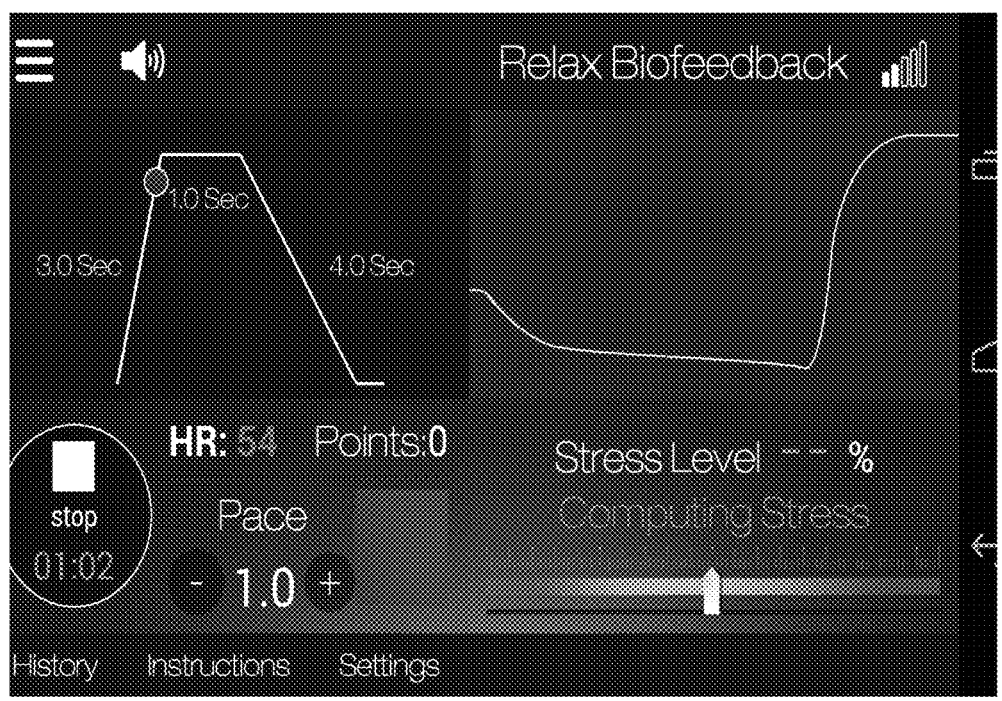

In some embodiments, after a period where sufficient data is acquire, the system calculates the initial inferred stress level (e.g., see FIG. 9)

Figure 10A:
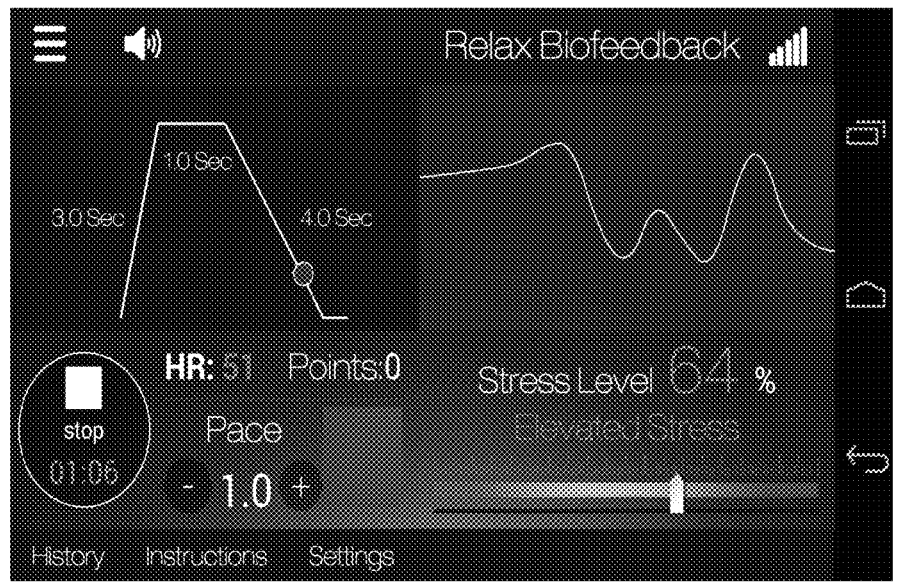
Figure 10B:
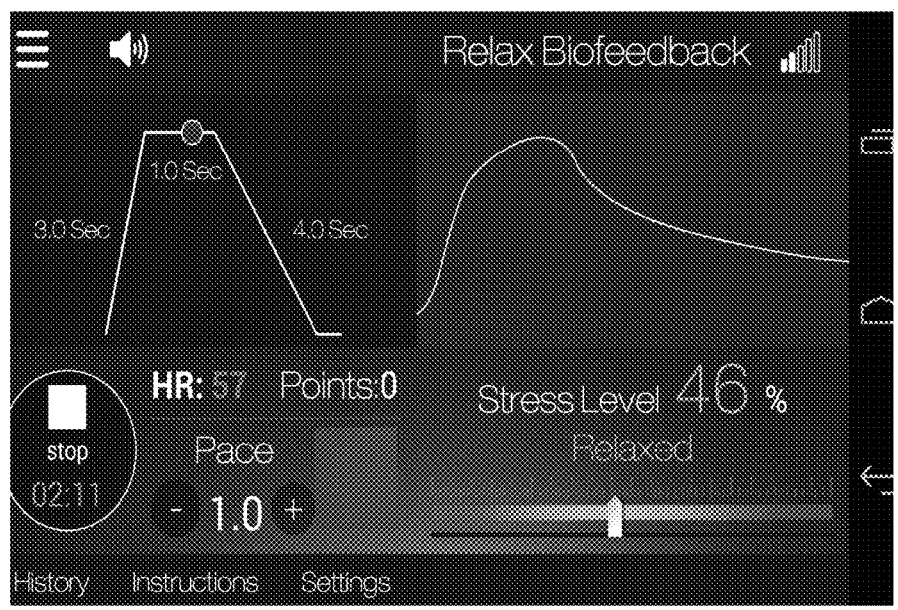
Figure 10C:
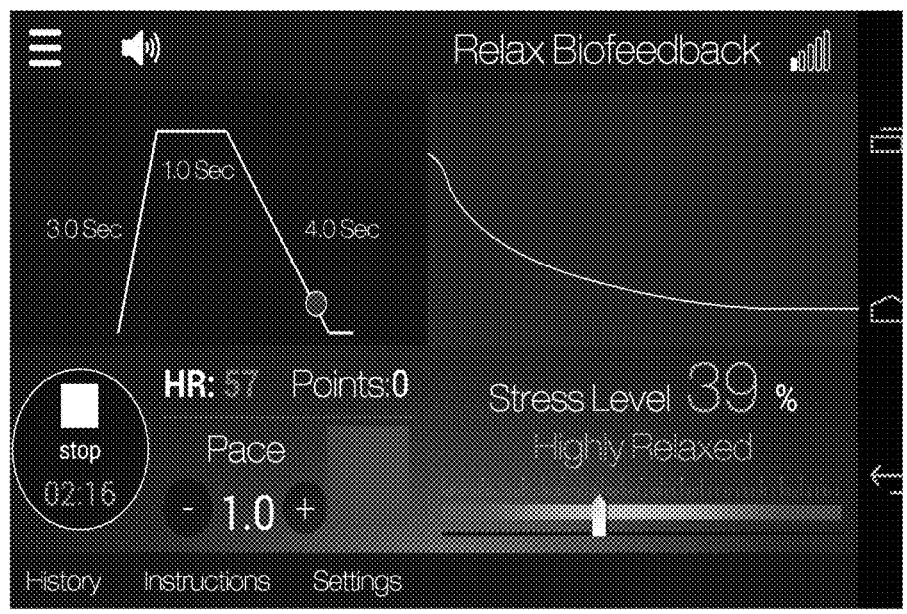

In some embodiments, an initial inferred stress level is indicated and is being updated in real time, reflecting the changes in the inferred stress level based on how the body responds to the personalized breathing exercise (e.g., FIGS. 10A-C.)

Figure 11:
FIGS. 11 and 12 are embodiments of the system of the present invention, showing screenshots that can be displayed on a device.

In some embodiments, whenever the signal quality is insufficient, the system can provide a message of low signal quality, such as FIG. 11.

In some embodiments, the indicators of stress level are typically according to the stress level percentages. In the non-limiting example above, the range between 40-50% is relaxed, below 40% is Highly Relaxed and above 50% is Stressed or Elevated Stress.

In a non-limiting example, the stress function calculation includes the following:

In some embodiments, during the Stress Biofeedback exercise the Stress Function is composed by a combination of heart coherence, heart rate minimum and maximum variation and heart rate.

1.1 Coherence

The coherence is a measure of how synchronous the heart rate variation is with the breathing. In some embodiments, the coherence is computed from the heart rate variability power spectrum, by looking at the percentage of the power that falls within the breathing frequency.

The breathing frequency (bf) is computed as:

$$bf=1/(inhale+hold+exhale)$$

where inhale, hold, and exhale are expressed in seconds and bf in Hz.

Figure 12:
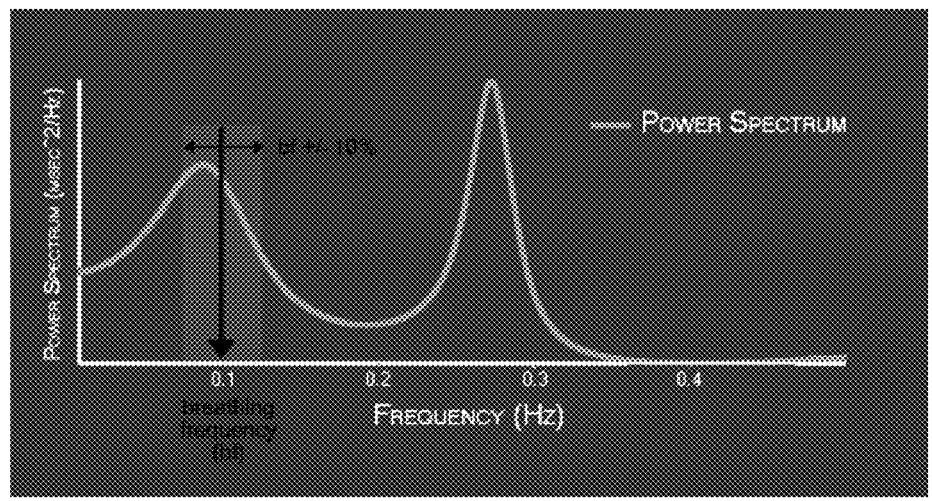
Figure 13A:
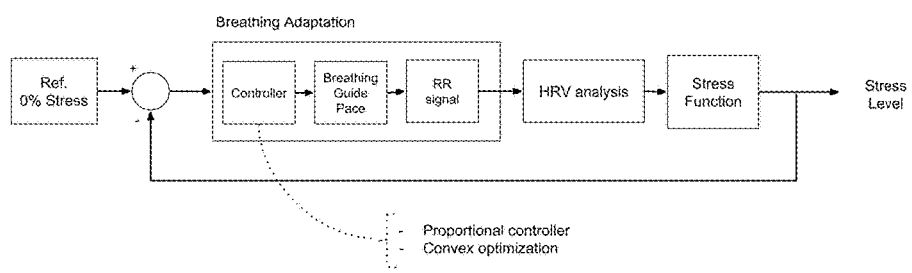
FIG. 13A is an embodiment of the system of the present invention, showing a feedback loop that can be used.
Figure 13B:
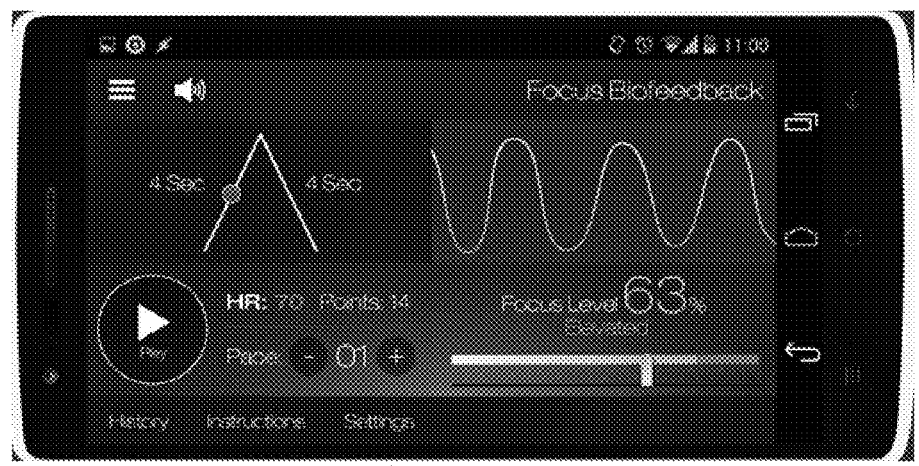
FIGS. 13B-13E are embodiments of the system of the present invention, showing screenshots that can be displayed on a device.
Figure 13C:
Figure 13D:
Figure 13E:
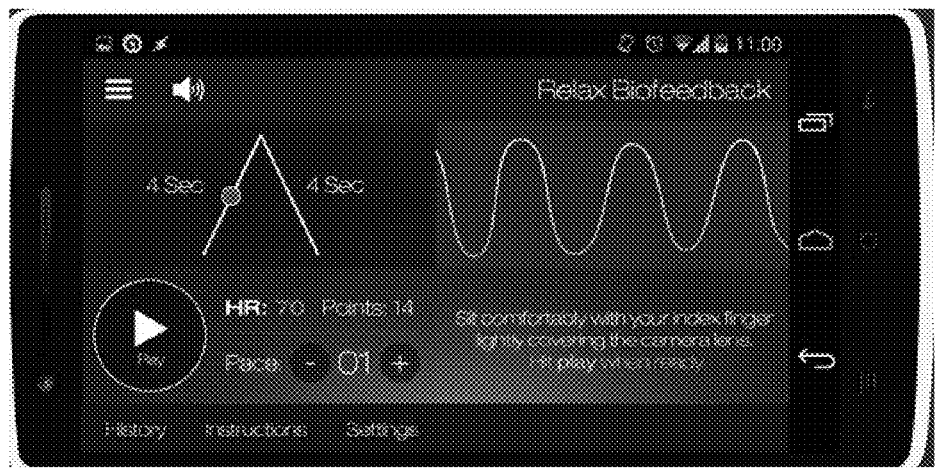

In an exemplary embodiment, Heart Rate Variability—Power Spectrum can be calculated. In some embodiments, the coherence is computed by integrating the area corresponding to the breathing frequency and normalizing it the total power (e.g., FIG. 12).

In some embodiments, the power corresponding to the breathing frequency $P_{bf}$ is computed on the area surrounding bf, defined as bf±10%, as shown in figure above. In some embodiments, the coherence is finally normalized as:

$$coherence=P_{bf}/P_{total}$$

where $P_{total}$ is the total power (area under the orange curve in figure above. Coherence is thus a normalized value, ranging from 0 to 1.

In some embodiments, the contribution of coherence to the stress function, in percentage, assumes that a coherence of 0 corresponds to 100% stress and a coherence of 0.8 (80% of the total power) corresponds to 0% stress. In some embodiments, this translates to $$P\text{coherence} = -125 \times \text{coherence} + 100$$

The numbers: −125 and 100 are fixed values which correspond to the parameters used in the linearization of the coherence values. The linearization maps each value of coherence into a 0:100 value.

1.2 Variation

In some embodiments, during a breathing cycle, the heart rate increases during inspiration (mediated by the sympathetic nervous system) and decreases during expiration (by the inhibition of the sympathetic nervous system/activation of the parasympathetic nervous system).

In some embodiments, in a healthy young adult the exhale/inhale ratio (E:I) of the maximum/minimum interbeat intervals (time, in seconds, between successive beats), respectively, is known to be at least 1.17 during relaxed breathing. In some embodiments, assuming that a E:I ratio of 1 (no variation) corresponds to 100% stress and a E:I of 1.7 corresponds to 0% stress, the contribution of heart rate variation to the stress function, in percentage, becomes:

$$P\text{E:I} \approx -143 \times \text{E:I} + 242$$

The values: −143 and 242 are fixed values which correspond to the parameters used in the linearization of variation values. The linearization maps each value of variation into a 0:100 value.

Heart Rate

In some embodiments, the contribution of the instantaneous heart rate (HR) to the stress function assumes that a resting heart rate of 60 bpm corresponds to 0% stress and a resting heart rate of 110 bpm corresponds to 100% stress. In some embodiments, each new heart rate value is mapped to a percentage of stress as $$P\text{HR} = 2 \times \text{HR} - 120$$

Stress Function

In some embodiments, the global Stress Value is updated, on each iteration, taking into account the previous Stress Value (SV) and the new estimation (Temporary Stress Level). In some embodiments, the Temporary Stress Level (TSL) is computed by linearly combining the 3 independent measures (all of them limited to a [0-100] range) as $$\text{TSL} = 0.4 \times P\text{coherence} + 0.4 \times P\text{E:I} + 0.2 \times P\text{HR}$$

In some embodiments, the computation of the final Stress Level (SL) suffers a bias that favors lower values along the time. In some embodiments, the bias, and the final SL computation is given by, as a non-limiting example:

$$\text{SL} = \text{TSL} \times 0.5 + \text{SV} \times 0.5 \text{ if TSL} < \text{SV}$$

$$\text{SL} = \text{TSL} \times 0.35 + \text{SV} \times 0.65 \text{ if TSL} > \text{SV}$$

Points System

In some embodiments, the Points system is based on the heart rate variation measure, explained in the previous section. In some embodiments, here, a breathing cycle is defined as an inspiration/hold/expiration as shown by the breathing indicator. In some embodiments, the user is awarded one point every time that the E:I ratio is higher than 1.2, indicating that he successfully followed the breathing guide, inducing a large heart rate variability. In some embodiments, other pointing system could be used, with the principle being that the user is awarded for success.

Personalization of Breathing Pattern

In some embodiments, the diagram below is detailing the closed loop control system.

In some embodiments, basically, the present invention starts with a certain Stress Value which is compared with a reference (our "objective, which is 0% stress). In some embodiments, the difference between the objective and the observed value is fed to the controller, which will adapt the breathing pace. In some embodiments, this new pace will be reflected on the HRV and on the Stress Value, thus closing the loop.

In some embodiments, regarding the controller, it can implement control blocks with different degrees of complexity, for example using convex optimization to find a "f(pace)=stress" function but it can use a simple controller. In a non-limiting example, one could use different pace values and then do small adjustments in the pace in the "direction" (lower/higher) that return a lower stress level. In some embodiments, effectively, this is a simplified version of a Proportional Integrative Derivative (PID) controller.

In some embodiments, one could also alter the breathing curves, for example randomly show the user on the first few times that he uses the app, and then we stick to the one where he gets the lowest stress levels, see, e.g., FIGS. 13A-E.

In some embodiments, in this screen you can either press the play button and start the operation (by placing your finger on the back of the phone on its camera and flash). In some embodiments, on the top left you see instructions where the left of the triangle instruct you to inhale and the right part of the triangle instruct you to exhale. In some embodiments, the red dot location guides you what to do, according to its location (inhale or exhale). In some embodiments, the wave on the right part of the screen is the heart rate variability on a rolling basis. In some embodiments, in the middle of the screen, there is a depiction of the Heart rate (HR) and the number of points in the game that the user gained. In some embodiments, there are many games that could be utilized, in the illustration here, the gamification is based on a biofeedback game whereby the user is guided to breath according to a breathing pattern and points are gained wherever an HRV wave is maximized at an inhalation. Points are gained if the user is tracking the instructions correctly (by following the ball).

Figure 14A:
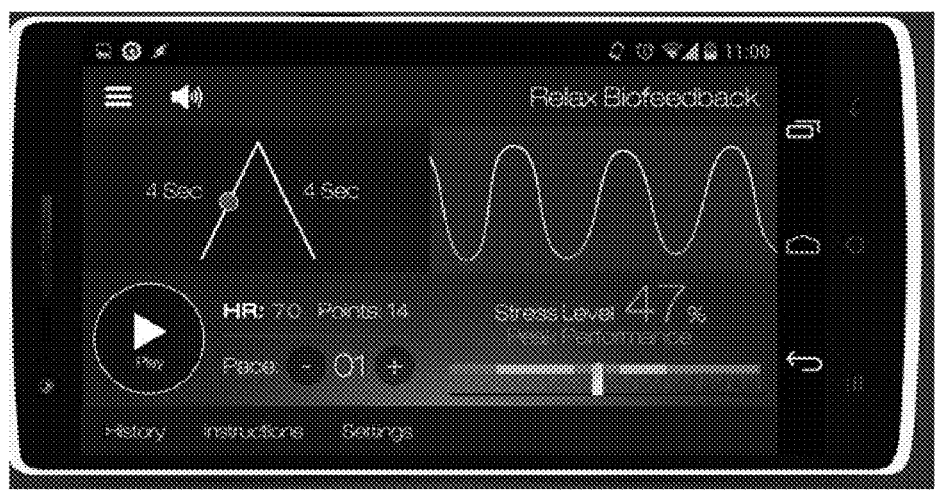
FIGS. 14A-14B, 15, 16A-16E, and 17A-17H are embodiments of the system of the present invention, showing screenshots that can be displayed on a device.
Figure 14B:
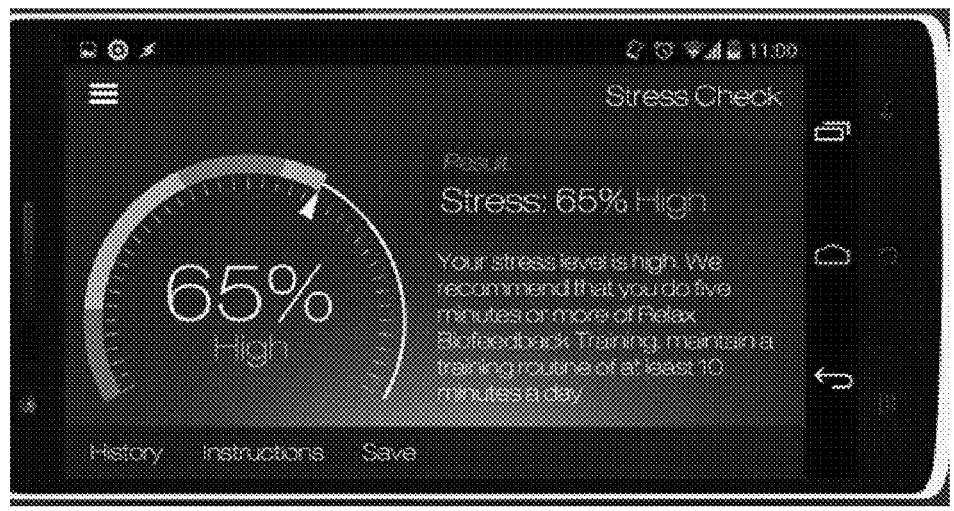

Some illustrated embodiments are shown in FIGS. 14A-B.

Figure 15:
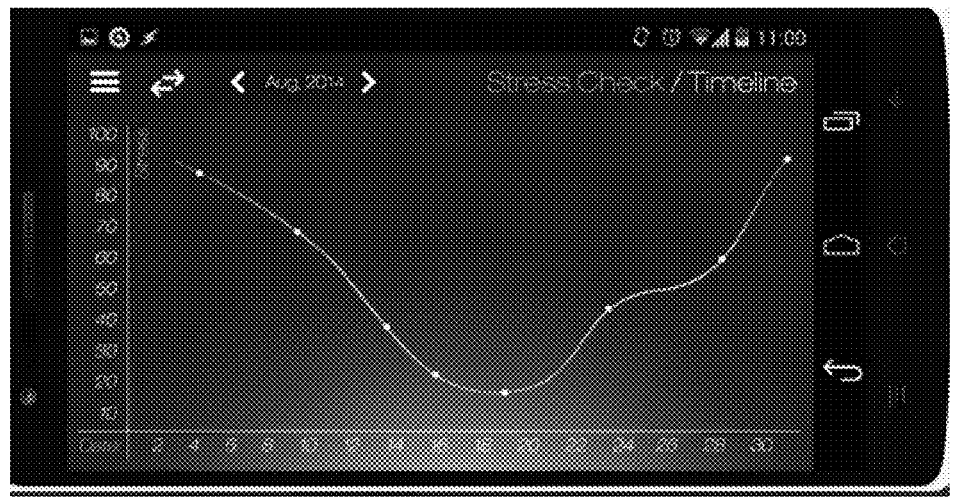
Figure 16A:
Figure 16B:
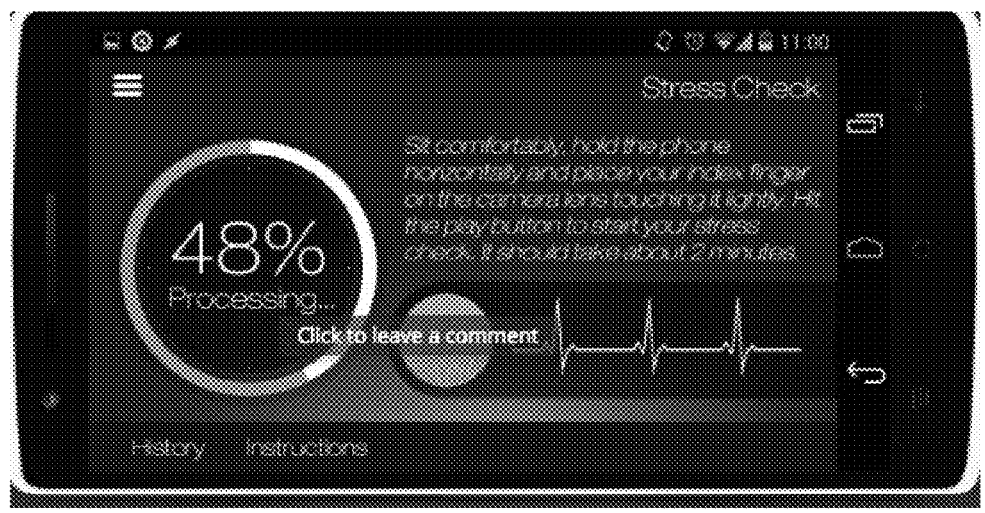
Figure 16C:
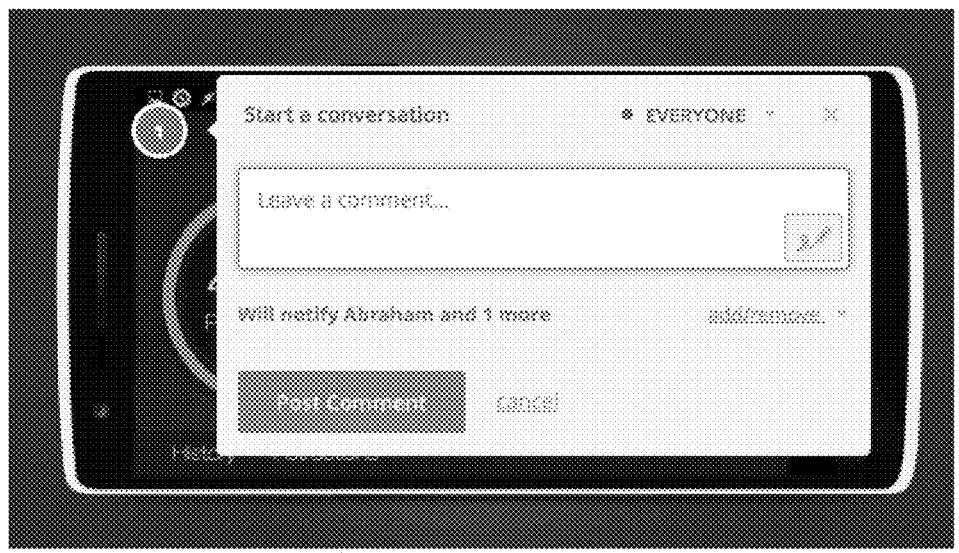
Figure 16D:
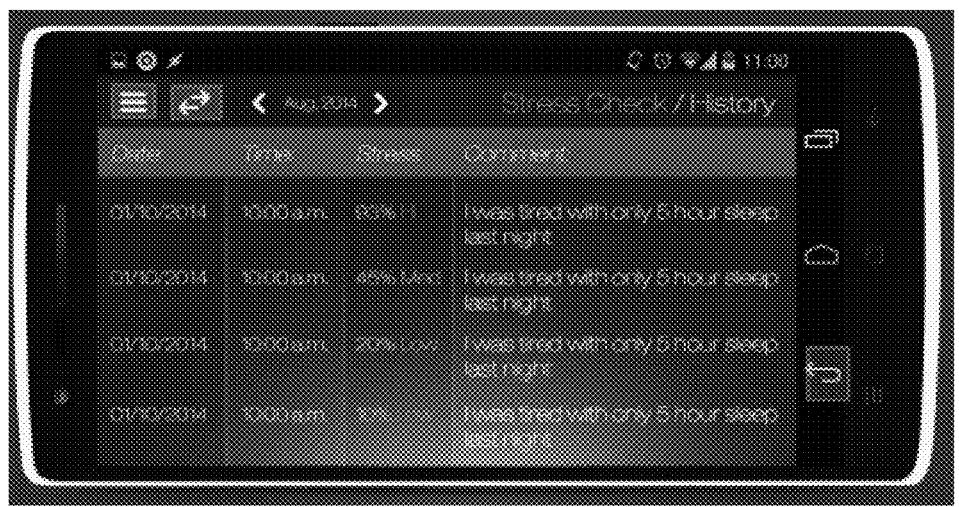
Figure 16E:
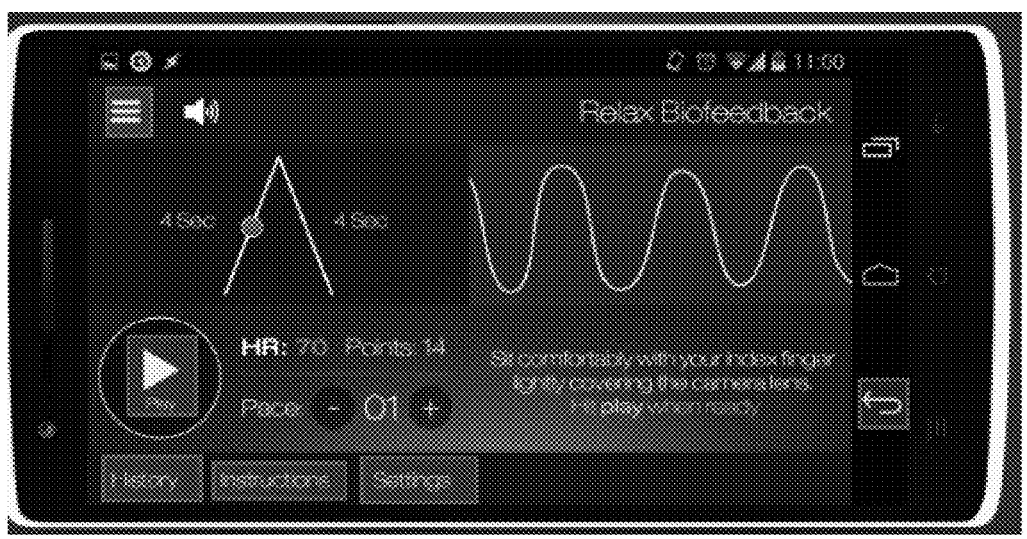
Figure 17A:
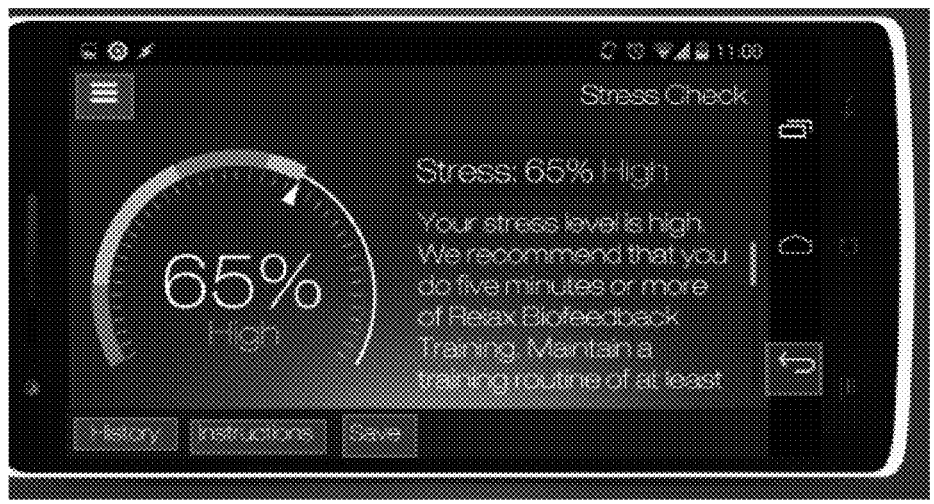
Figure 17B:
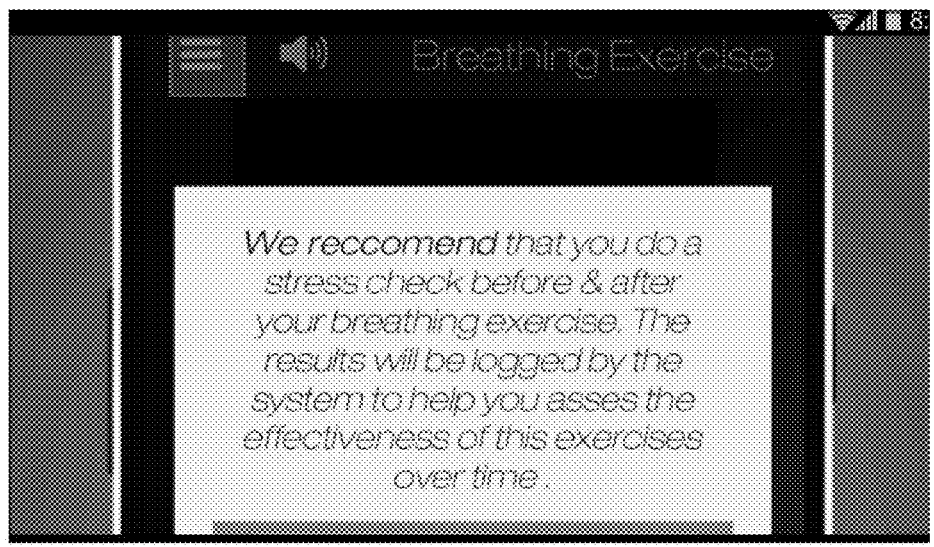
Figure 17C:
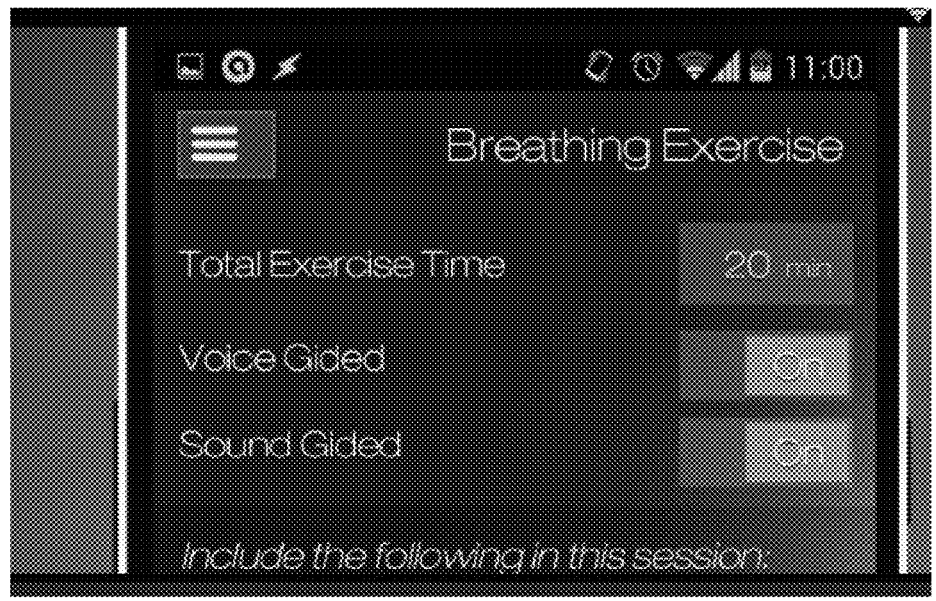
Figure 17D:
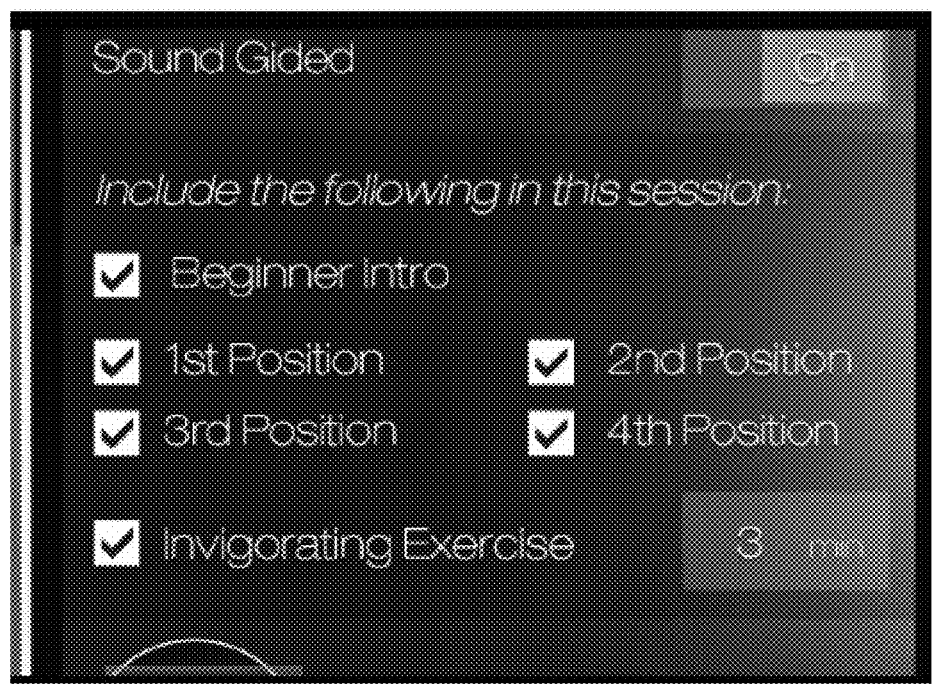
Figure 17E:
Figure 17F:
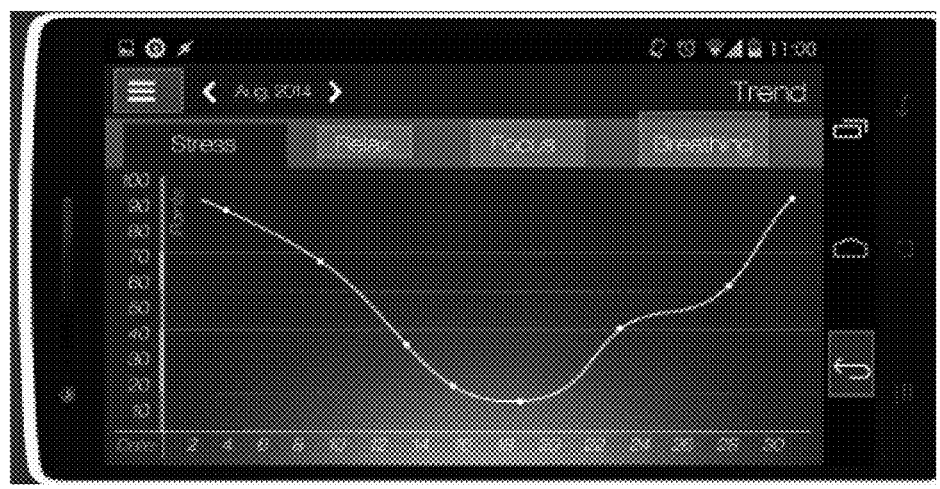
Figure 17G:
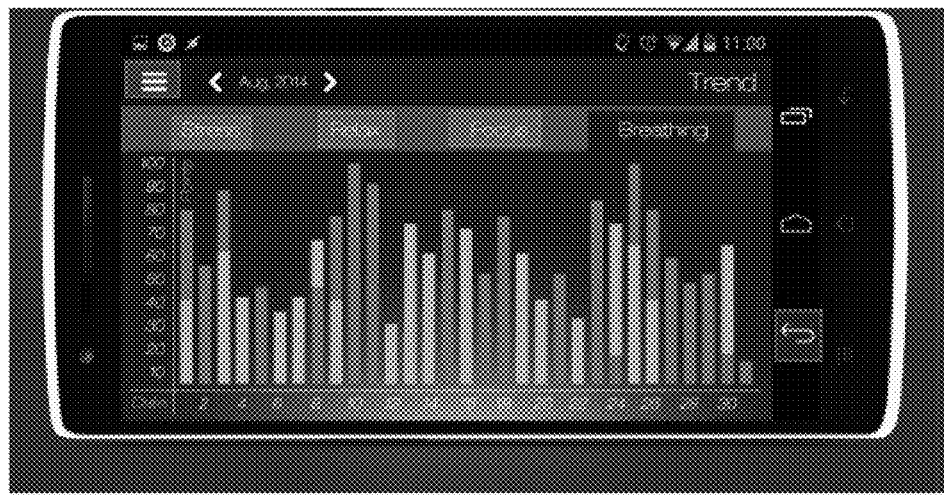
Figure 17H:
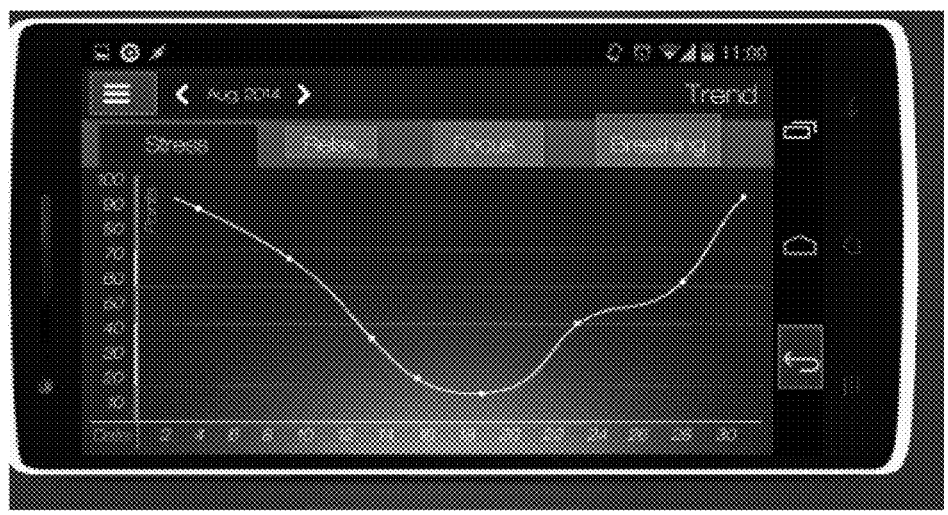

In some embodiments, peak performance shows the minimum stress level that was achieved during a session. In some embodiments, in general, the lower the stress level, the more relaxed a person is (see, e.g., FIG. 15).

In some embodiments, the present invention also maintains graphing capabilities so the user can view his/her progress over time (see, e.g., FIGS. 16A-E).

In some embodiments, in addition to the biofeedback drills, the user can choose which of the selection of breathing exercise he would like to include in his regimen. For a non-limiting example, the first, second, third and fourth position and the invigorating exercise described in the diagrams (e.g., FIGS. 17A-H).

A Method of Calculating Stress Level from the PPG Signal

The algorithm described herein estimates stress levels based on the deviations of the Heart Rate around normal levels and on the ratio between Low and High frequency components of the HRV.

The problem at hand is the high variance between successive measurements of stress levels, with the system presenting very low consistency across users and measurements.

In order to find the origin of this unwanted variation and a possible solution, the following formulation investigates a)

if the acquired RR signal is robust enough and b) if the HRV features are robust enough to guarantee results consistency.

Signal Acquisition and Quality

In order to keep the smartphone processor load low, the instantaneous heart rate signal (RR) acquired is not filtered or interpolated.

The following analyses were all performed using the algorithms described before, namely PPG acquisition and processing, RR signal construction and HRV features computation. In this section, the data was acquired with the user sitting in a comfortable position, without moving while watching TV.

The first step on the analysis of signal quality was to implement and test the influence of a linear interpolation algorithm, setting the RR signal to a known, fixed sampling rate. Several sampling rates were tested, namely 2, 5 and 10 Hz.

Figure 18A:
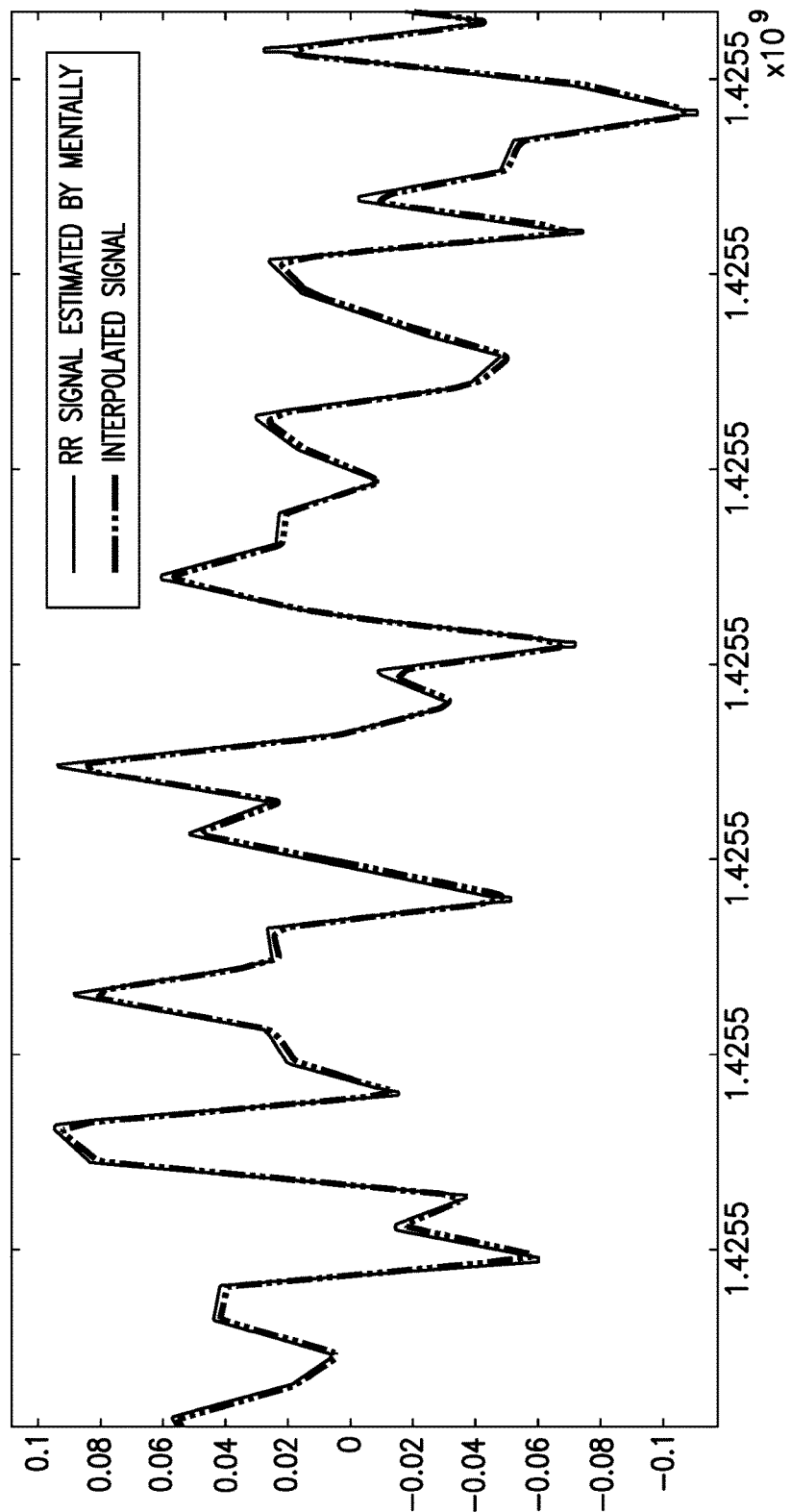
FIG. 18A is an embodiment of the system of the present invention, showing a comparison of two minutes of data from the original and interpolated RR signal.
Figure 18B:
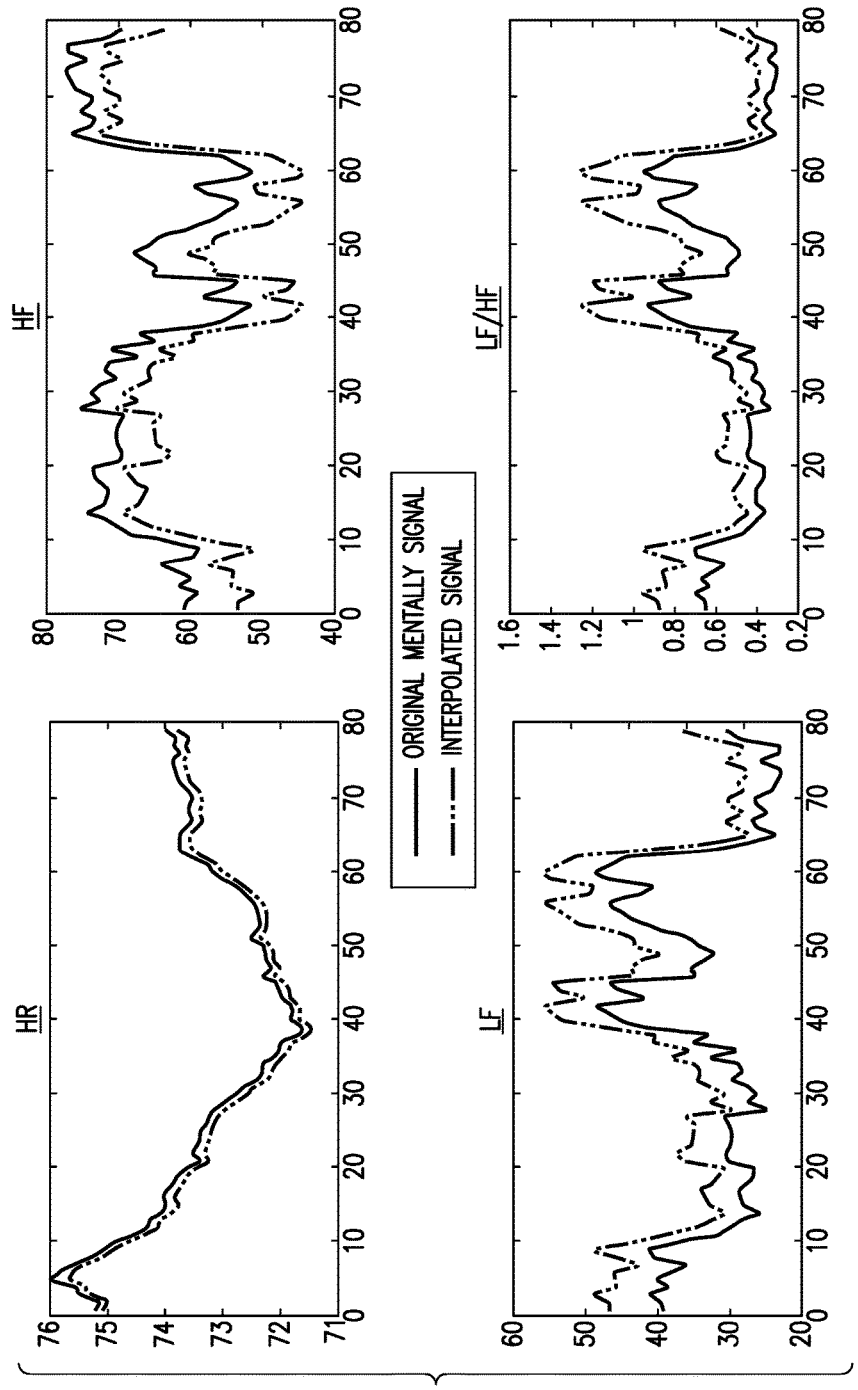
FIG. 18B is an embodiment of the system of the present invention, showing a comparison of features computed from the original and interpolated RR signal. The variations are consistent on the two different signals. The features shown are the Heart Rate (top left) the High Frequency components (top right) the Low Frequency components (bottom left) and Lf/Hf ratio (bottom right).

FIGS. 18A and 18B compare two minutes of the different RR signals (original and interpolated (5 Hz)) and the respective HRV features. It can be seen that the results are consistent on the two signals. Spectral analysis of signals with sharp edges, as the ones shown in FIG. 18A, typically lead to strong components on the high frequency bands, thus masking the true spectrum. The second operation performed on the RR signal was a Low-pass filtering step, in order to smooth the signal prior to spectral analysis.

Figure 19:
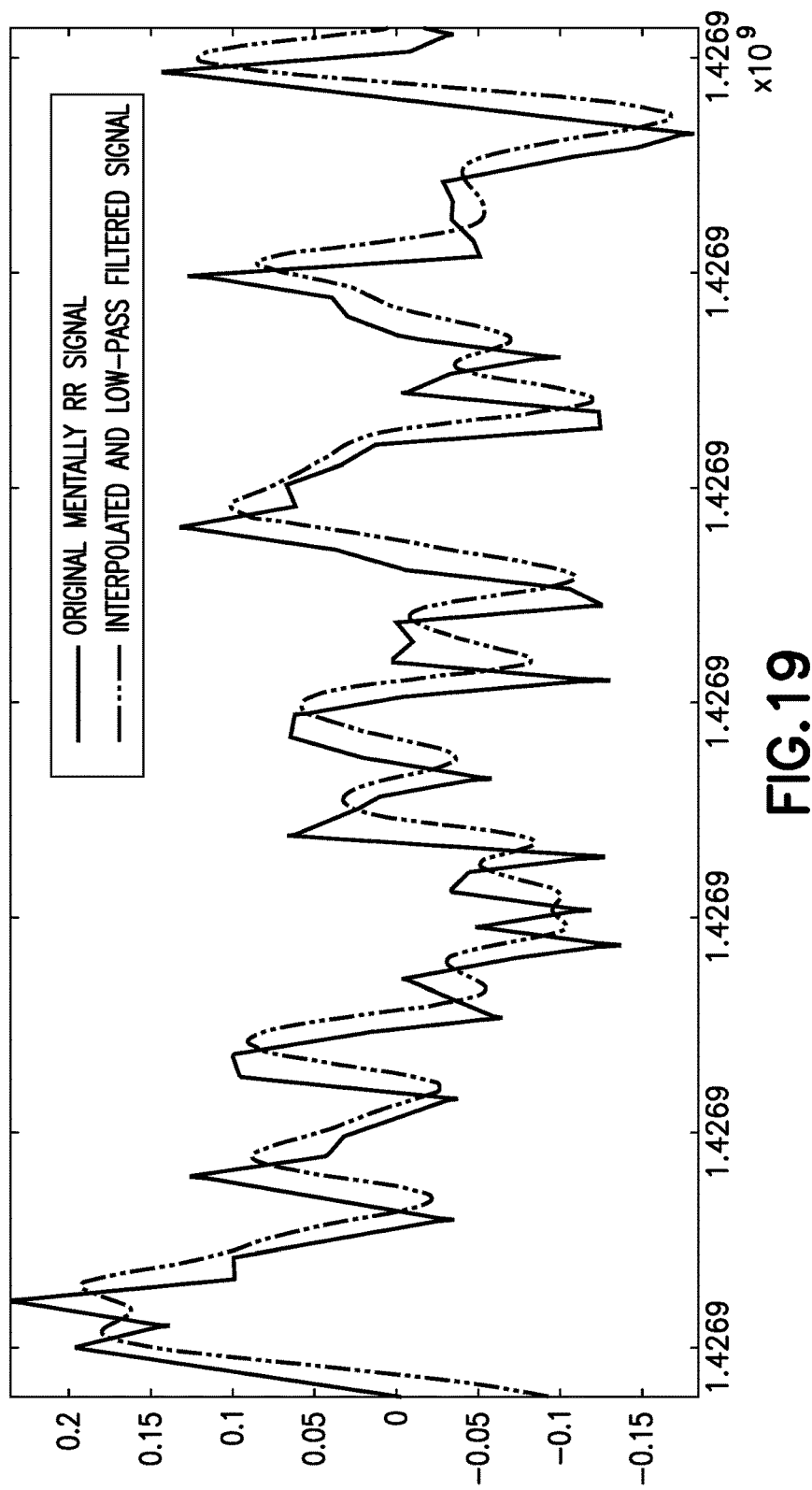
FIG. 19 is an embodiment of the system of the present invention, showing a comparison of the original RR signal and a version of the same signal interpolated and filtered.

FIG. 19 shows the comparison of the two signals, the filtering effect is evident on the green line as well as the delay introduced by the $2^{nd}$ order filter. However the morphology of the two signals remains consistent.

Figure 20:
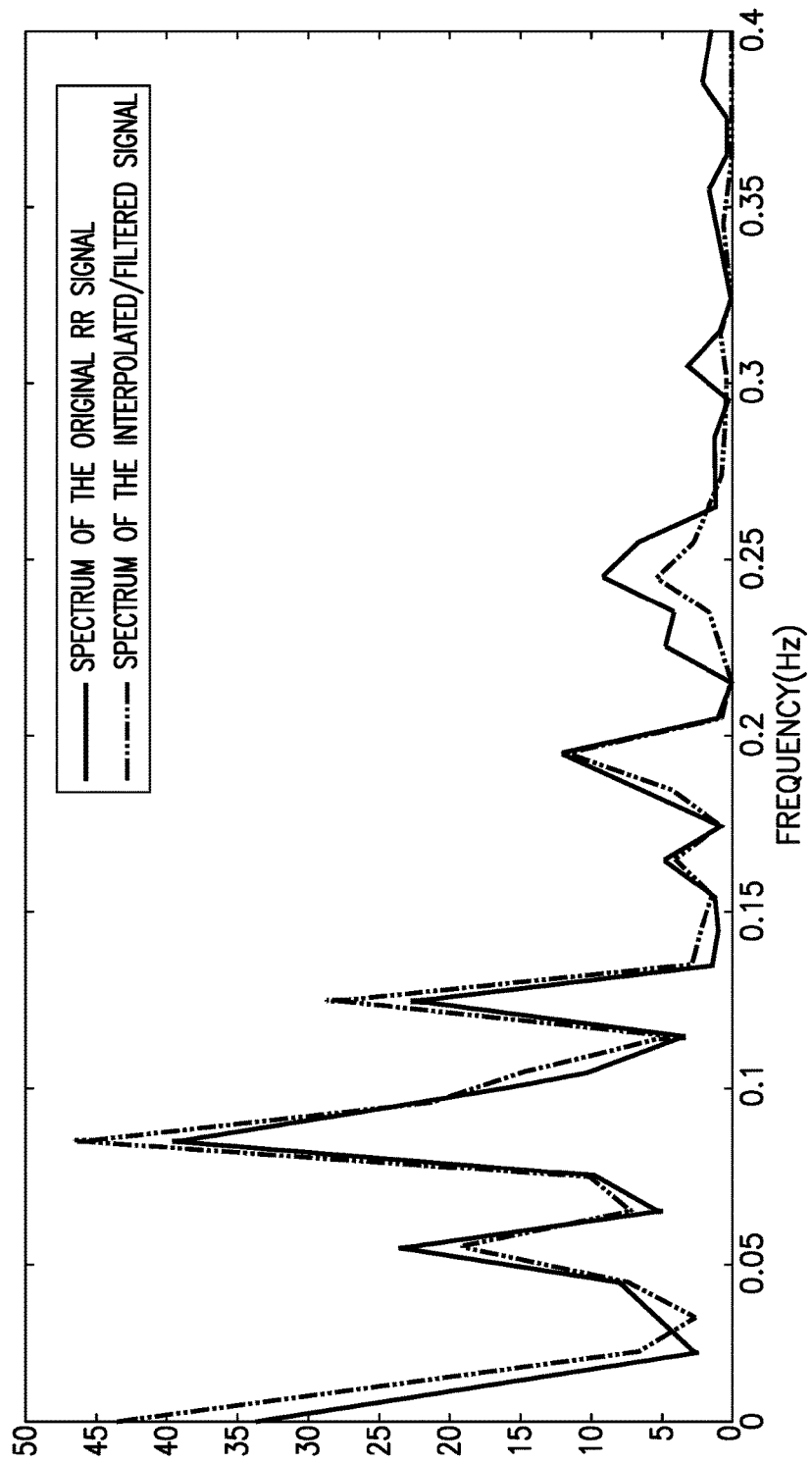
FIG. 20 is an embodiment of the system of the present invention, showing a comparison of the normalized spectrums of the two signals.

The influence of the interpolation and filtering steps is theoretically most noticeable on the signal spectrum. FIG. 20 compares the normalized HRV spectrum obtained from two minutes of the original RR signal based on the previous calculation and from the same signal after being interpolated and filtered.

The two spectrums show similarity, showing that frequency derived features will be similar to both signals. Without being bound by theory, the similarity of the two spectrums may be due to the spectrum estimation algorithm, which is robust on the estimation of spectrums from unevenly sampled signals.

Figure 21:
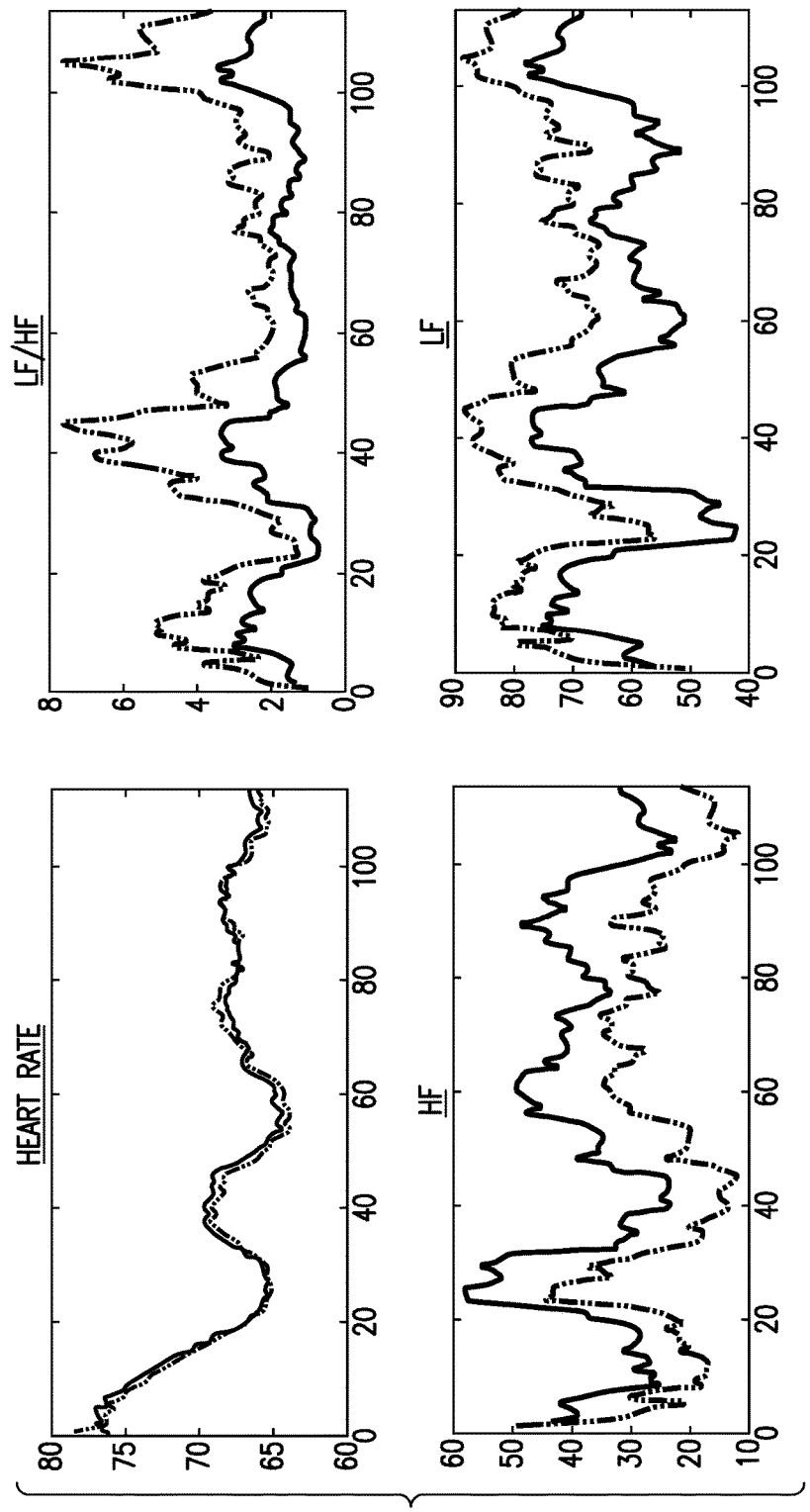
FIG. 21 is an embodiment of the system of the present invention, showing a comparison of 4 different features. The temporal evolution of the features from the two signals is similar with the exception of a scaling factor.

Finally, FIG. 21 compares four different features obtained from the original and interpolated/filtered signals. Once again, the temporal evolution is similar, with the exception of the scaling factor on the frequency features, due to the interpolation factor.

The results from FIG. 21 confirm that further processing on the RR signal from Mentally does not bring any significant advantage to the feature computation. However, a critical issue is the temporal variation on all the features. As explained before, the data used in the analysis was acquired with the user in a resting condition. Empirically, this should lead to very small variations on the features along the time, however this was not observed.

This temporal variation is natural and due to the regulatory mechanisms of the Autonomic Nervous System. Due to this permanent regulation, HRV analyses are normally averaged over long temporal windows (typically 5 minutes).

In the problem at hand, it is necessary to find a feature, or combination of features that are 1) directly related to stress levels and 2) exhibit minimum variations over short periods of time.

HRV Features for Short Term Stress Estimation

To determine the features for stress estimation, the following are considered: (1) Design a two part exercise capable to i) actively induce stress on a first phase and ii) promote relaxation on the second phase; (2) determine the HRV features that vary the most with the two considered states; (3) determine the HRV features that have low natural short term variations, and any combination thereof. Regarding point 1) the performed exercise consisted in i) 10 minutes of acquisition with the subject standing while solving Sudoku puzzles, both activities known to induce sympathetic responses via physical and psychological stress. The subject was then asked to ii) sit on a relaxed position on a couch, for 10 minutes, watching TV.

During both phases, the finger was properly placed on the smartphone's camera to ensure low signal noise.

The acquired data was processed and the mean and standard deviations were computed for the two periods of data. Features highly correlated with stress levels must exhibit higher variations on the mean value.

The considered features were the Heart Rate (HR), the High (HF) and Low (LF) frequency components of the HRV, the Lf/Hf ratio, the standard deviation of the RR (SDNN) interval over the considered time window, the minimum (MIN) and maximum (MAX) RR values on the considered time window, the breathing frequency (BR freq), the power associated to the breathing frequency (BR power) and finally, the percentage of RR samples over 50 ms (PNN 50).

The features were computed using a sliding window with 90 seconds (one and a half minutes).

Finally, in order to determine the variation on each feature caused by natural fluctuations, the normalized standard deviation was computed. The normalized standard deviation is obtained by dividing the standard deviation of the feature vector by its mean. The normalization step allows different features to be compared and lower standard deviations mean that the feature has a low tendency to drift or oscillate over low periods of time. The table below summarizes the obtained results. The percentage of variation on the mean value of each feature is marked in ITALICS. All features have relatively high variation, with the exception of the breathing rate. The higher variations are present on the Breathing Power (during relaxation the most evident frequency on the spectrum is the breathing frequency), the Lf/Hf ratio and the SDNN.

Regarding the short term natural fluctuations, the values UNDERLINED show the average normalized standard deviation on the two phases of the exercise. The lower variations are observed on the HR and MIN and MAX values.

Some selected features are those with high italicized values and low underlined values. The selected features for the integration on the algorithm are:

Heart Rate, already present on the algorithm, shows a relatively high difference between stress states and low short term variation.

The Lf/Hf ratio which is a "standard" feature on stress estimation and already used on the algorithm. Although it has high natural fluctuations, it is highly correlated with stress levels since it reflects the joint activity of the sympathetic and parasympathetic nervous systems.

The SDNN with large average differences between stress states and low natural fluctuations.
The breathing power
The PNN50

TABLE 1

| | Feature | | | | | |
|---|---|---|---|---|---|---|
| | HR | | | HF | | |
| | Mean | Stdev | Norm. Stdev | Mean | Stdev | Norm. Stdev |
| Standing | 84.49 | 1.87 | 0.0222 | 35 | 10.5 | 0.29 |
| Relaxed | 61.2 | 1.56 | 0.0255 | 48.88 | 10.52 | 0.21 |
| | 27.57 | | 0.02 | 39.66 | | 0.25 |

| | Feature | | | | | |
|---|---|---|---|---|---|---|
| | MIN | | | MAX | | |
| | Mean | Stdev | Norm. Stdev | Mean | Stdev | Norm. Stdev |
| Standing | 0.62 | 0.00278 | 0.0446 | 0.8 | 0.0359 | 0.0444 |
| Relaxed | 0.85 | 0.07 | 0.0702 | 1.08 | 0.0530 | 0.046 |
| | 37.10 | | 0.06 | 35.00 | | 0.05 |

| | Feature | | | | | |
|---|---|---|---|---|---|---|
| | LF/HF | | | SDNN | | |
| | Mean | Stdev | Norm. Stdev | Mean | Stdev | Norm. Stdev |
| Standing | 2.1 | 0.92 | 0.44 | 0.05 | 0.005 | 0.094 |
| Relaxed | 1.12 | 0.41 | 0.36 | 0.07 | 0.0126 | 0.1484 |
| | 46.67 | | 0.40 | 40.00 | | 0.12 |

| | Feature | | | | | |
|---|---|---|---|---|---|---|
| | BR Power | | | PNN50 | | |
| | Mean | Stdev | Norm. Stdev | Mean | Stdev | Norm. Stdev |
| Standing | 18.5 | 0.0478 | 0.2583 | 0.19 | 0.0393 | 0.2051 |
| Relaxed | 32 | 0.0775 | 0.325 | 0.25 | 0.0184 | 0.0889 |
| | 72.97 | | 0.29 | 31.58 | | 0.15 |

| | Feature | | | | | |
|---|---|---|---|---|---|---|
| | LF | | | BR freq | | |
| | Mean | Stdev | Norm. Stdev | Mean | Stdev | Norm. Stdev |
| Standing | 64 | 10.5 | 0.16 | 0.24 | 0.0676 | 0.2724 |
| Relaxed | 51.11 | 10.52 | 0.2 | 0.23 | 0.0304 | 0.1187 |
| | 20.14 | | 0.18 | 4.17 | | 0.20 |

Each of these features is an independent variable on a stress function, multiplied by suitable weights.

The stress function is expressed as: [0.1*lf/hf+0.3*Heart_Rate+0.2*SDNN+0.2*coherence+0.2*pnn50]

The weighted values of Table 1 are calculated using the weights as detailed below:
0.1=Lf/Hf
0.3=heart rate
0.2=SDNN
0.2=coherence
0.2=pnn50

Each feature (e.g., Lf/Hf, heart rate, SDNN, coherence, pnn50) is linearized to obtain a value from 0 to 100. The linearization is a typical fitting to a line in the form y=m*x+b where suitable values for y and x were obtained experimentally and m and b were obtained solving the system of equations. When a new value for x arrives, the equation is solved and returns a y value on that line. If the y value is larger than 100 or smaller than 0 it is set to 100 and 0 respectively. This process is repeated to all features on the stress function.

Figure 22A:
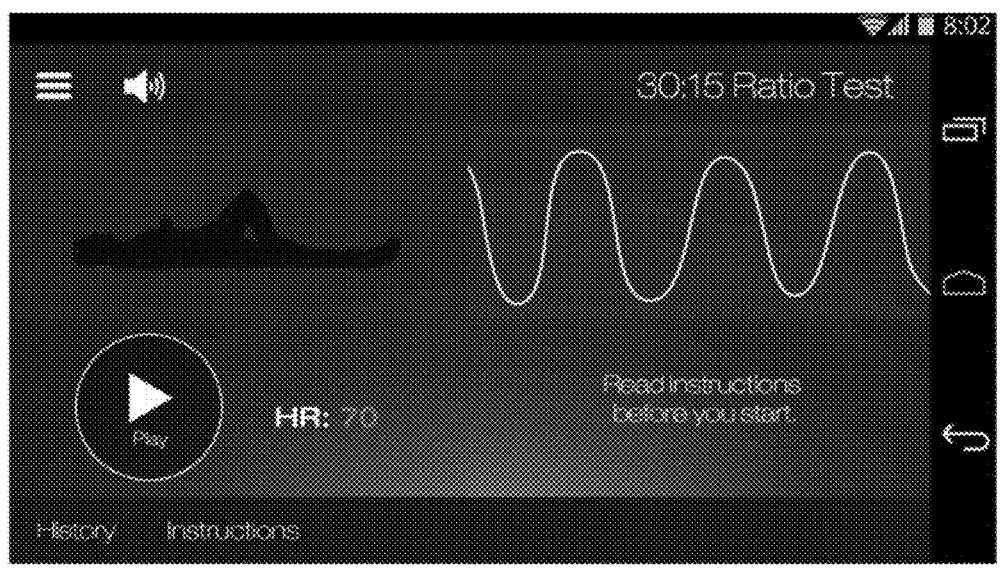
FIGS. 22A and 22B are embodiments of the system of the present invention, showing screenshots that can be displayed on a device.
Figure 22B:
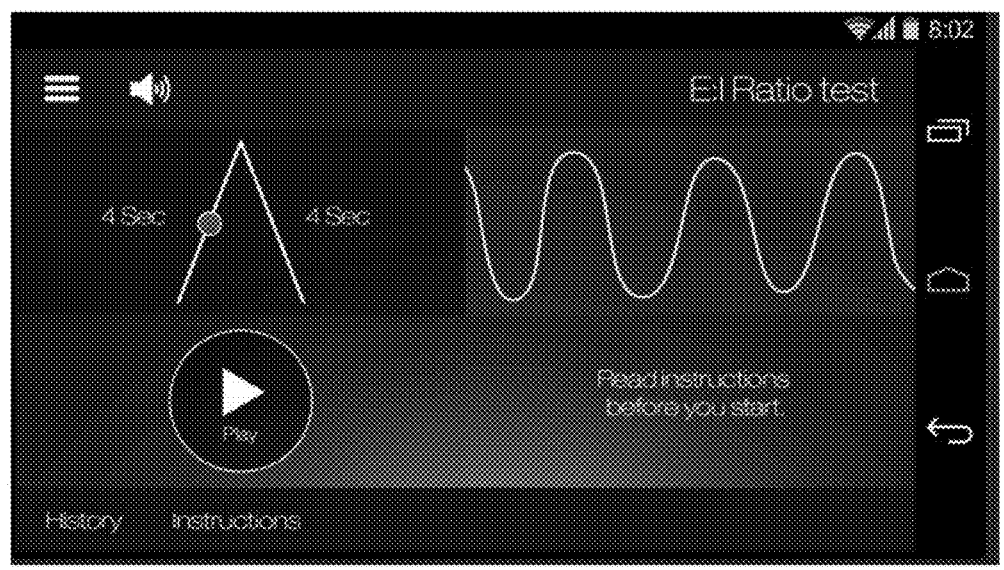

FIGS. 22A-B show non-limiting instructions for the CAN tests described above.

Heart Rate Variability

The rhythmical contraction of the heart is controlled by a group of specialized cells, the Sinoatrial Node (SAN), positioned on the wall of the heart's right atrium. Although all of the heart's cells have the ability to rhythmically generate action potentials, it is the SAN that initiates each cardiac contraction.

In the absence of any neurohumoral influence (nervous or hormonal) the SAN generates approximately 100-120 action potentials per minute, resulting on an equivalent Heart Rate (HR). However, a resting healthy human is likely to have a slower HR of around 70-80 bpm due to the modulation of the SAN firing rate by the innervations of both sympathetic and parasympathetic branches of the Autonomous Nervous System (ANS).

In addition to the direct neural innervation of the heart, other processes responsible to influence the heart rate include the indirect effect of the sympathetic system through the release of adrenomedullary catecholamines and the fluctuations induced by the respiratory-related mechanical stretch of the SAN.

The chronotropic control of the heart is performed by the ANS. The instantaneous HR is thus considered a manifestation of both the (antagonistic) effects of the parasympathetic and the sympathetic nerves through permanent changes in neurotransmitters levels. During rest, both autonomic divisions are thought to be tonically active with the parasympathetic effects achieving dominance, thus lowering the natural frequency of the pacemaker.

Figure 23:
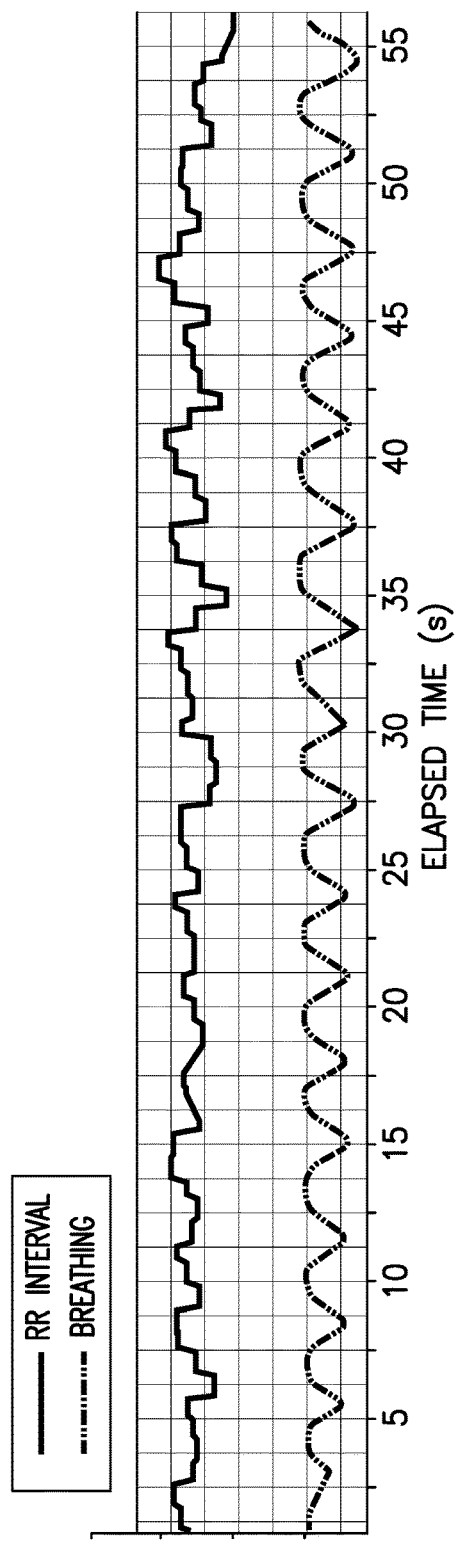
FIG. 23 is an embodiment of the system of the present invention, showing approximately one minute of acquired data, documented from a healthy subject under resting conditions.

FIG. 23, as a non-limiting example, shows approximately one minute of R-to-R and Respiratory Inductance Plethysmography (RIP) data, acquired from a healthy subject under resting conditions. R-to-R, or briefly, RR data, is given by the interval between successive R peaks from the QRS complexes detected on the ECG, where the QRS complex is the combination of three of the graphical deflections seen on a typical electrocardiogram which corresponds to the depolarization of the right and left ventricles of the human heart. It is often interpreted as the inverse of the instantaneous HR.

It is clear that the RR (blue line) varies around a mean, representing the fine tuning of the beat-to-beat control mechanisms, this oscillation is partially correlated with the breathing waveform. The natural oscillation in the interval between consecutive heartbeats has received many names, including RR variability, RR tachogram and cycle length variability, but the most commonly accepted term to this phenomenon is HRV.

FIG. 23: Approximately one minute of RR (blue line) and Breathing data (green line), acquired on a relaxed subject. The RR interval has a natural variation, due to regulatory mechanisms mediated by the ANS. During rest, this variation is highly correlated with the breathing waveform.

Several methods for the analysis of HRV are described in the literature, they are commonly divided in Time Domain Methods, including statistical and geometric measures and Frequency Domain Methods. The periodic components of heart variability tend to aggregate around typical frequency bands, three major components are identifiable. The Very Low Frequencies (VLF) in the interval 0.0-0.015 Hz, the Low Frequencies (LF), in the interval 0.015-0.15 Hz and the High Frequencies, 0.15-0.4 Hz. The spectrum of the arterial Blood Pressure variability also exhibits two main frequency bands, highly correlated with the LF and HF components of the HRV. Without being bound by theory, it is believed that in the closed-loop circulatory system, these components correspond to vasomotor activity (LF band) and to the respiratory activity oscillation (HF band).

The two LF and HF HRV frequency bands are thus intimately connected with the activity of the two branches of the ANS. The HF component is a reliable marker of vagal (parasympathetic) activity. Exercises of controlled respiration, cold stimulation of the face, and rotational stimuli have been shown to increase the HF components, conditions that can increase vagal activity.

Figure 24A:
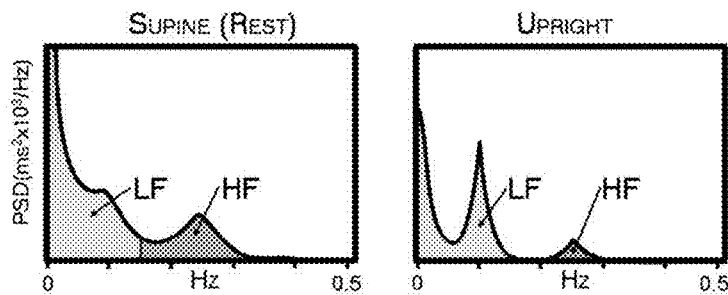
FIGS. 24A and 24B is an embodiment of the system of the present invention, showing a spectral analysis of the HRV on a healthy subject performing an active orthostatic test.
Figure 24B:
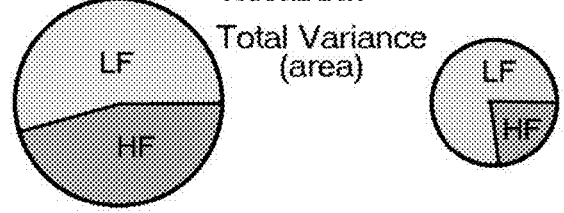

FIG. 24: Spectral analysis of the HRV on a healthy subject performing an active orthostatic test. (FIG. 24A) The normalized power spectrum density (ms2×103/Hz) shows that in supine position the two components, LF and HF, have approximately similar powers. In the upright position the LF component predominates, appearing to have a power similar to the supine position. (FIG. 24B) The pie charts areas reflect the total variance on the HRV. This reveals a strong reduction of the HRV power in the upright position. Both LF and HF components are reduced, something not easily perceived in normalized units.

Origin of the Frequency Components

The frequency components of the HRV described in the previous section, are mainly attributed to the activity of the two branches of the ANS.

Vagus nerve activity can change heart rate substantially within one cardiac cycle, and the chronotropic effects decay almost completely within one cardiac cycle after cessation of vagal activity. A vagal burst has its maximum effect after approximately 0.5 seconds, with a return to baseline within ≈1 second. A sympathetic burst caused no effect for at least 1 second and its maximum expression was only verified 4 seconds later, followed by a 20 seconds relaxation time. Vagal and sympathetic responses could be characterized by low-pass filters, with an additional delay in the case of the sympathetic system. Vagal filter response was characterized as fast with little delay, with a corner frequency of ≈0.15 Hz and the sympathetic response as slow, with 1-2 seconds delay and a corner frequency of ≈0.015 Hz. These filter responses are consistent with the observations in humans, where the sympathetic system modulates the HR in frequencies under ≈0.15 Hz and parasympathetic system in frequencies between 0-0.5 Hz.

A possible explanation to the difference in the responses of the two systems is related to receptor processes and postsynaptic responses. A delay in the cardiac response to acetylcholine and norepinephrine may arise from processes subsequent to the binding of the agonist to the receptor. The linkage between muscarinic receptor activation and changes in ionic currents is mediated by signaling molecules located largely within the cell membrane, opposed to adrenergic stimulation, which is initiated in the membrane and requires a second-messenger activation (a protein kinase in the cytosol) which eventually sends a signal back to the membrane to change the ionic currents.

The emphasis for the physiological explanation of the different responses is usually placed on the speed of the process that initiates the responses, however, the processes that terminate the responses to the ANS stimuli might provide further answers, in particular the processes responsible for the removal of the released neurotransmitters.

The norepinephrine released by the sympathetic nerve endings is removed from the cardiac tissues much more slowly than the acetylcholine, released from the vagal terminals. As a consequence of the potential harmful effects associated with the slow removal of norepinephrine, the cardiac neural control system might have evolved such that the sympathetic nerves ordinarily release the norepinephrine at a slow rate. Hence, changes in sympathetic neural activity can alter cardiac behavior only slightly from beat to beat. Beatwise control of cardiac function would thus be negligible, regardless of how swiftly the sympathetic nerve impulse is transduced to a change in cardiac performance.

Illustrative Operating Environments

Figure 2:
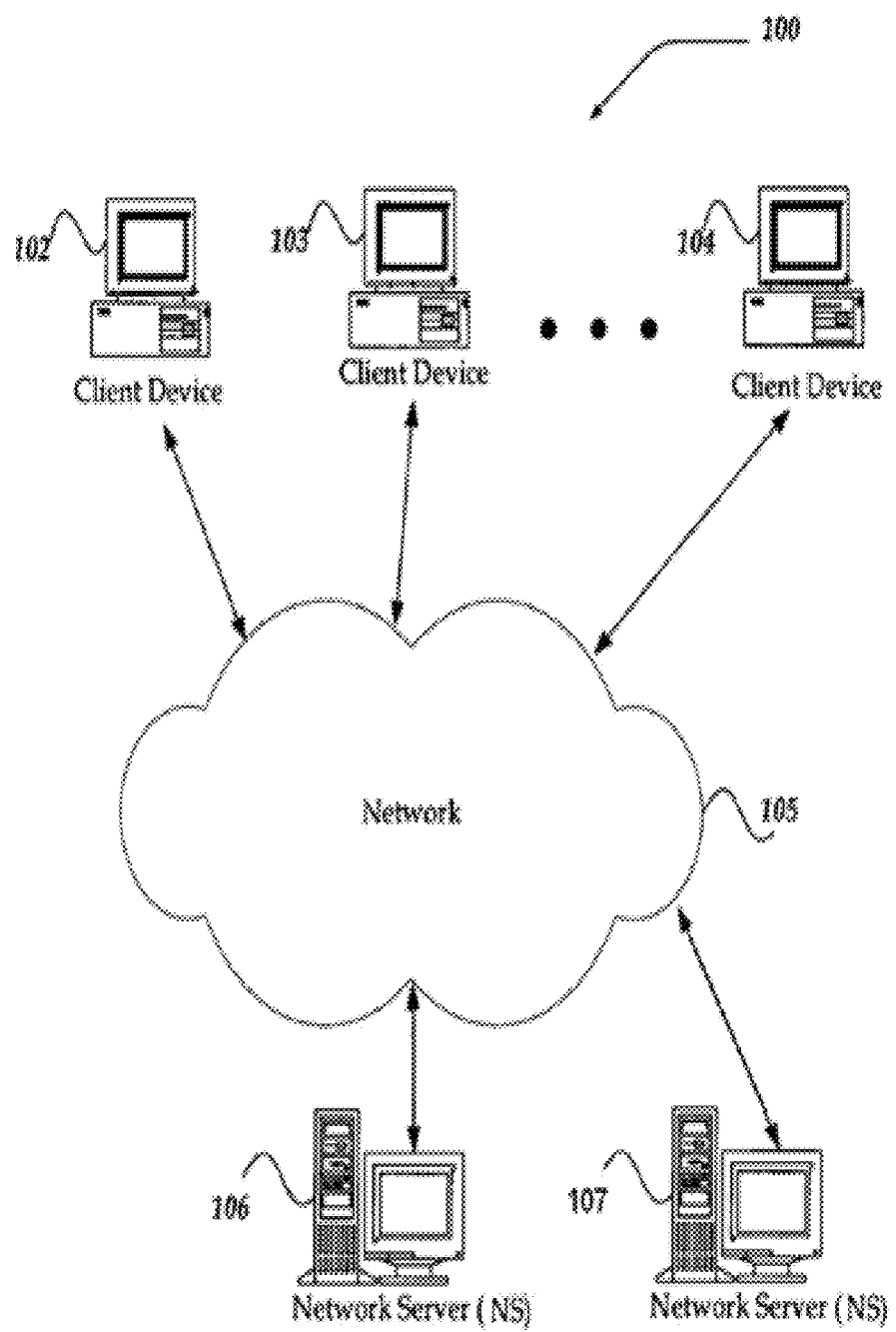
FIG. 2 illustrates an embodiment of the system of the present invention, showing network servers communicating with client devices by use of a network.

FIG. 2 illustrates one embodiment of an environment in which the present invention may operate. However, not all of these components may be required to practice the invention, and variations in the arrangement and type of the components may be made without departing from the spirit or scope of the present invention. In some embodiments, the system and method may include a large number of members and/or concurrent transactions. In other embodiments, the system and method are based on a scalable computer and network architecture that incorporates varies strategies for assessing the data, caching, searching, and database connection pooling. An example of the scalable architecture is an architecture that is capable of operating multiple servers.

In embodiments, members of the computer system 102-104 include virtually any computing device capable of receiving and sending a message over a network, such as network 105, to and from another computing device, such as servers 106 and 107, each other, and the like. In embodiments, the set of such devices includes devices that typically connect using a wired communications medium such as personal computers, multiprocessor systems, microprocessor-based or programmable consumer electronics, network PCs, and the like. In embodiments, the set of such devices also includes devices that typically connect using a wireless communications medium such as cell phones, smart phones, pagers, walkie talkies, radio frequency (RF) devices, infrared (IR) devices, CBs, integrated devices combining one or more of the preceding devices, or virtually any mobile device, and the like. Similarly, in embodiments, client devices 102-104 are any device that is capable of connecting using a wired or wireless communication medium such as a PDA, POCKET PC, wearable computer, and any other device that is equipped to communicate over a wired and/or wireless communication medium.

In embodiments, each member device within member devices 102-104 may include a browser application that is configured to receive and to send web pages, and the like. In embodiments, the browser application may be configured to receive and display graphics, text, multimedia, and the like, employing virtually any web based language, including, but not limited to Standard Generalized Markup Language (SMGL), such as HyperText Markup Language (HTML), a wireless application protocol (WAP), a Handheld Device Markup Language (HDML), such as Wireless Markup Language (WML), WMLScript, XML, JavaScript, and the like. In some embodiments, programming may include either Java, .Net, QT, C, C++ or other suitable programming language.

In embodiments, member devices 102-104 may be further configured to receive a message from another computing device employing another mechanism, including, but not limited to email, Short Message Service (SMS), Multimedia Message Service (MMS), instant messaging (IM), internet relay chat (IRC), mIRC, Jabber, and the like or a Proprietary protocol.

In embodiments, network 105 may be configured to couple one computing device to another computing device to enable them to communicate. In some embodiments, network 105 may be enabled to employ any form of computer readable media for communicating information from one electronic device to another. Also, in embodiments, network 105 may include a wireless interface, and/or a wired interface, such as the Internet, in addition to local area networks (LANs), wide area networks (WANs), direct connections, such as through a universal serial bus (USB) port, other forms of computer-readable media, or any combination thereof. In embodiments, on an interconnected set of LANs, including those based on differing architectures and protocols, a router may act as a link between LANs, enabling messages to be sent from one to another.

Also, in some embodiments, communication links within LANs typically include twisted wire pair or coaxial cable, while communication links between networks may utilize analog telephone lines, full or fractional dedicated digital lines including T1, T2, T3, and T4, Integrated Services Digital Networks (ISDNs), Digital Subscriber Lines (DSLs), wireless links including satellite links, or other communications links known to those skilled in the art. Furthermore, in some embodiments, remote computers and other related electronic devices could be remotely connected to either LANs or WANs via a modem and temporary telephone link. In essence, in some embodiments, network 105 includes any communication method by which information may travel between client devices 102-104, and servers 106 and 107.

Figure 3:
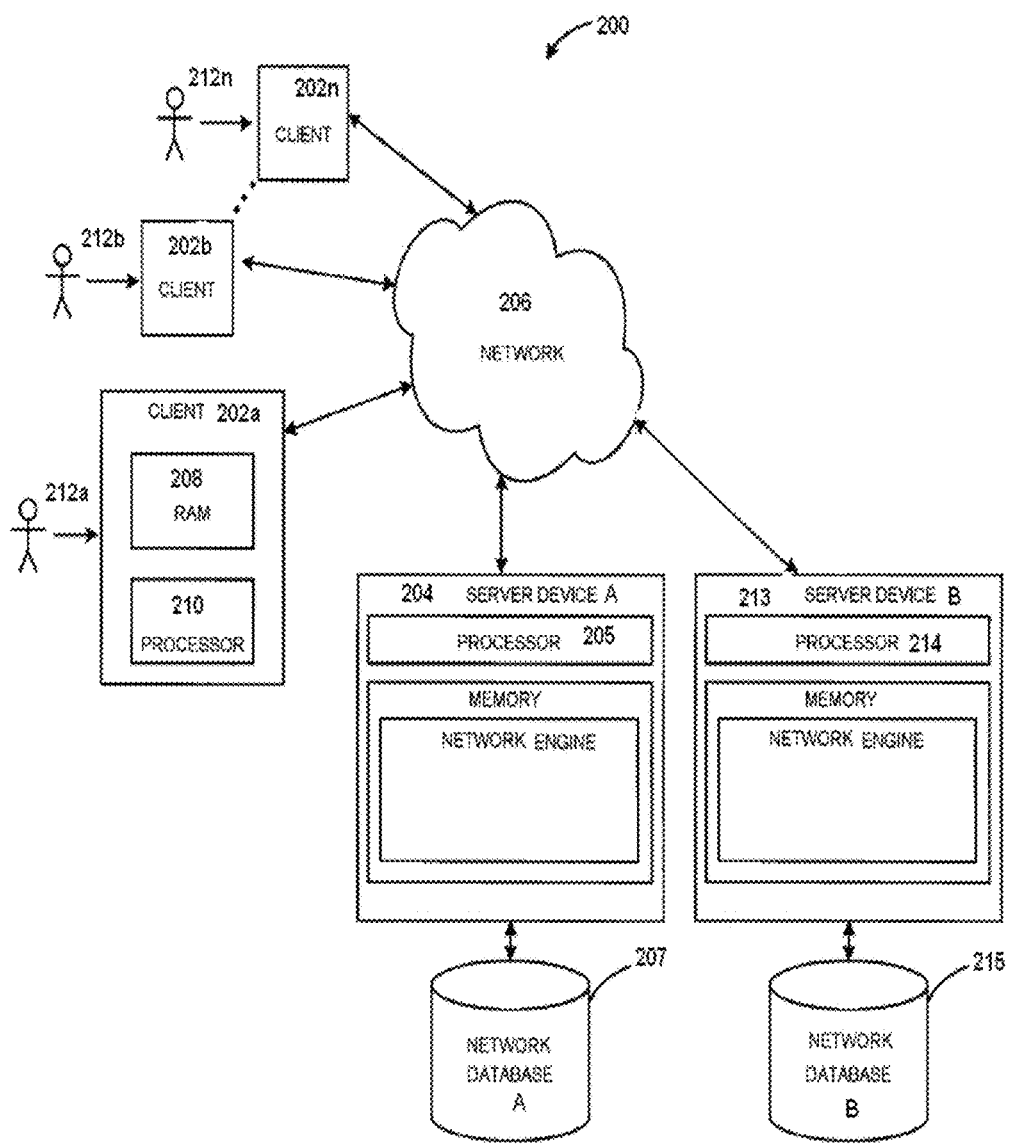
FIG. 3 illustrates an embodiment of the system of the present invention, showing a computer and network architecture that supports the inventive system.

FIG. 3 shows another exemplary embodiment of the computer and network architecture that supports the method and system. The member devices 202a, 202b thru 202n shown each at least includes a computer-readable medium, such as a random access memory (RAM) 208 coupled to a processor 210 or FLASH memory. The processor 210 may execute computer-executable program instructions stored in memory 208. Such processors comprise a microprocessor, an ASIC, and state machines. Such processors comprise, or may be in communication with, media, for example computer-readable media, which stores instructions that, when executed by the processor, cause the processor to perform the steps described herein. Embodiments of computer-readable media may include, but are not limited to, an electronic, optical, magnetic, or other storage or transmission device capable of providing a processor, such as the processor 210 of client 202a, with computer-readable instructions. Other examples of suitable media may include, but are not limited to, a floppy disk, CD-ROM, DVD, magnetic disk, memory chip, ROM, RAM, an ASIC, a configured processor, all optical media, all magnetic tape or other magnetic media, or any other medium from which a computer processor can read instructions. Also, various other forms of computer-readable media may transmit or carry instructions to a computer, including a router, private or public network, or other transmission device or channel, both wired and wireless. The instructions may comprise code from any computer-programming language, including, for example, C, C++, Visual Basic, Java, Python, Perl, and JavaScript. The aforementioned examples are, of course, illustrative and not restrictive.

Figure 4:
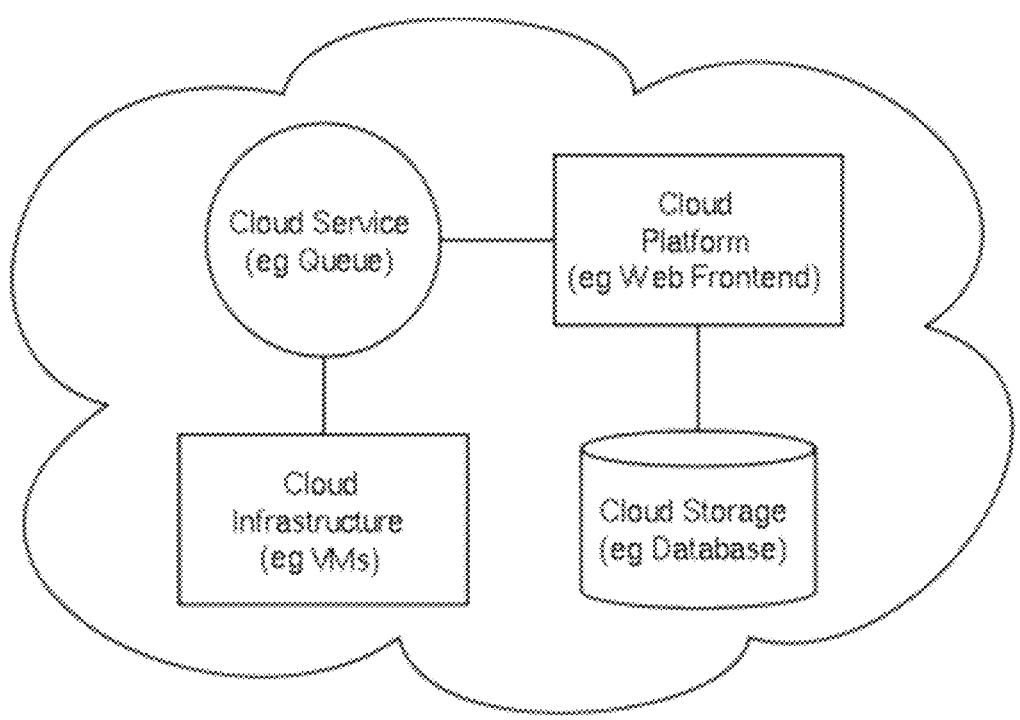
FIG. 4 illustrates an embodiment of the inventive system of the present invention, showing a cloud system supporting the inventive system.
Figure 5:
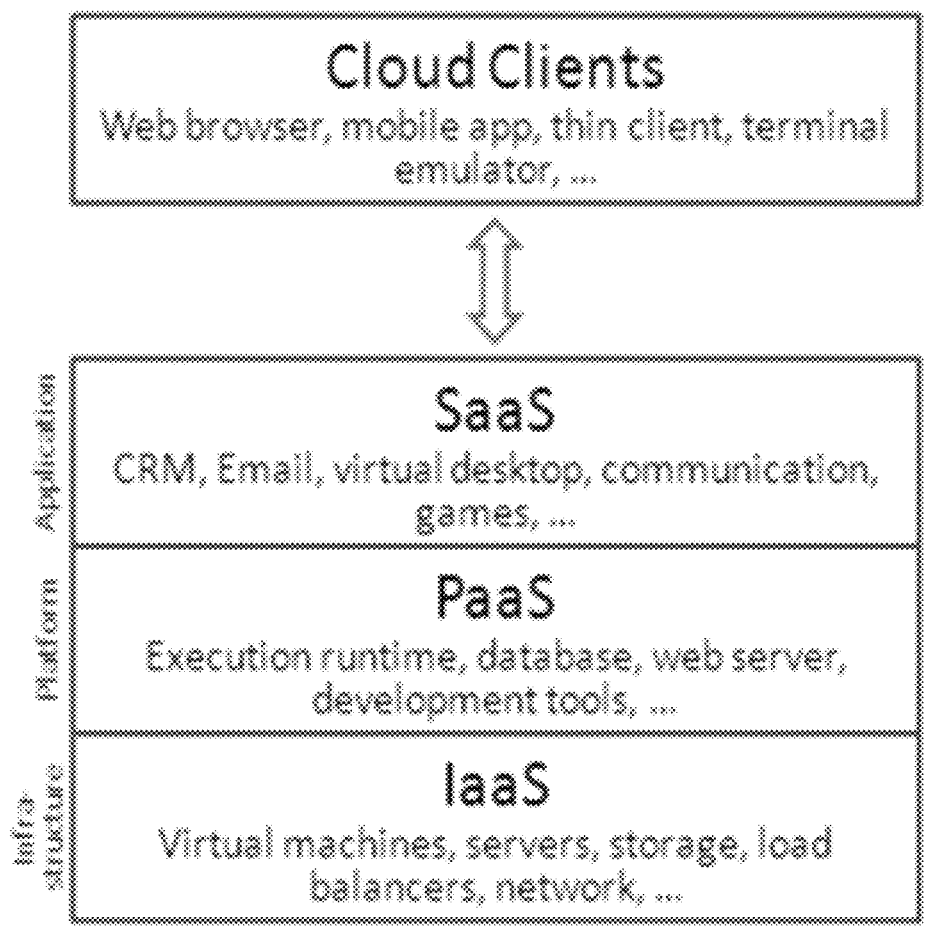
FIG. 5 illustrates an embodiment of the system of the present invention, showing the cloud systems supporting the inventive system and allowing a delivering and receiving of information to and/or from cloud clients.

For purposes of the instant description, the terms "cloud," "Internet cloud," "cloud computing," "cloud architecture," and similar terms correspond to at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). In some embodiments, the instant invention offers/manages the cloud computing/architecture as, but not limiting to: infrastructure a service (IaaS), platform as a service (PaaS), and software as a service (SaaS). FIGS. 4 and 5 illustrate schematics of exemplary implementations of the cloud computing/architecture.

Member devices 202a-n may also comprise a number of external or internal devices such as a mouse, a CD-ROM, DVD, a keyboard, a display, or other input or output devices, which can be specifically programmed with personalized stress management software. Examples of client devices 202a-n may be personal computers, digital assistants, personal digital assistants, cellular phones, mobile phones, smart phones, pagers, digital tablets, laptop computers, Internet appliances, and other processor-based devices. In general, a client device 202a may be any type of processor-based platform that is connected to a network 206 and that interacts with one or more application programs. Client devices 202a-n may operate on any operating system capable of supporting a browser or browser-enabled application, such as Microsoft™, Windows™, or Linux. The client devices 202a-n shown may include, for example, personal computers executing a browser application program such as Microsoft Corporation's Internet Explorer™, Apple Computer, Inc.'s Safari™, Mozilla Firefox, and Opera. Through the client devices 202a-n, users, 212a-n communicate over the network 206 with each other and with other systems and devices coupled to the network 206. As shown in FIG. 1B, server devices 204 and 213 may be also coupled to the network 206. The personalized stress management software can be configured to be shown on at least one graphical user interface.

In some embodiments, the term "mobile electronic device" may refer to any portable electronic device that may or may not be enabled with location tracking functionality. For example, a mobile electronic device can include, but is not limited to, a mobile phone, Personal Digital Assistant (PDA), Blackberry™, Pager, Smartphone, or any other reasonable mobile electronic device. For ease, at times the above variations are not listed or are only partially listed, this is in no way meant to be a limitation.

In some embodiments, the terms "proximity detection," "locating," "location data," "location information," and "location tracking" as used herein may refer to any form of location tracking technology or locating method that can be used to provide a location of a mobile electronic device, such as, but not limited to, at least one of location information manually input by a user, such as, but not limited to entering the city, town, municipality, zip code, area code, cross streets, or by any other reasonable entry to determine a geographical area; Global Positions Systems (GPS); GPS accessed using Bluetooth™; GPS accessed using any reasonable form of wireless and/or non-wireless communication; WiFi™ server location data; Bluetooth™ based location data; triangulation such as, but not limited to, network based triangulation, WiFi™ server information based triangulation, Bluetooth™ server information based triangulation; Cell Identification based triangulation, Enhanced Cell Identification based triangulation, Uplink-Time difference of arrival (U-TDOA) based triangulation, Time of arrival (TOA) based triangulation, Angle of arrival (AOA) based triangulation; techniques and systems using a geographic coordinate system such as, but not limited to, longitudinal and latitudinal based, geodesic height based, cartesian coordinates based; Radio Frequency Identification such as, but not limited to, Long range RFID, Short range RFID; using any form of RFID tag such as, but not limited to active RFID tags, passive RFID tags, battery assisted passive RFID tags; or any other reasonable way to determine location. For ease, at times the above variations are not listed or are only partially listed, this is in no way meant to be a limitation.

In some embodiments, near-field wireless communication (NFC) can represent a short-range wireless communications technology in which NFC-enabled devices are "swiped," "bumped," "tap" or otherwise moved in close proximity to communicate. In some embodiments, NFC could include a set of short-range wireless technologies, typically requiring a distance of 10 cm or less.

In some embodiments, NFC may operate at 13.56 MHz on ISO/IEC 18000-3 air interface and at rates ranging from 106 kbit/s to 424 kbit/s. In some embodiments, NFC can involve an initiator and a target; the initiator actively generates an RF field that can power a passive target. In some embodiment, this can enable NFC targets to take very simple form factors such as tags, stickers, key fobs, or cards that do not require batteries. In some embodiments, NFC peer-to-peer communication can be conducted when a plurality of NFC-enable devices within close proximity of each other.

In some embodiments, the instant invention provides for a computer-implemented method, including: providing, to a user, in real time, by at least one specialized computing device being specifically programmed with wellbeing management software, at least one personalized breathing instruction via a graphical user interface displayed on the at least one specialized computing device, where the at least one personalized breathing instruction includes at least: (i) a first indication identifying a first duration for inhaling, and (ii) a second indication identifying a second duration for exhaling; receiving, in real time, by the at least one specialized programmed computing device, user sensor data from at least one heart rate sensor being associated with the user, determining, in real time, by the at least one specialized programmed computing device, user heart rate variability of the user (user HRV), based, at least in part, on the user sensor data, automatically calculating, by the at least one specialized programmed computing device, based on the user HRV, a parameter status percentage, based, at least in part, on a weighted sum of a plurality of user-related parameters, including: (1) a first parameter identifying a Low frequency/High frequency ratio of the user, (2) a second parameter identifying a standard deviation of an instantaneous heart rate signal (SDNN) of the user, (3) a third parameter identifying a heart rate of the user, (4) a fourth parameter identifying a pnn50 of the user, and (5) a fifth parameter identifying a coherence of the user, so as to result in a calculated value of between 0.1-100%; providing, to the user, in real time, by the at least one specialized programmed computing device, based on the parameter status percentage, at least one personalized breathing recommendation being configured to modify the parameter status percentage, where the at least one breathing recommendation includes: (i) a first breathing indication identifying a first adjustment to a breathing rate of the user, (ii) a second breathing indication identifying a second adjustment to a breathing pattern of the user, (iii) or any combination thereof. In some embodiments, the method further includes a third indication identifying a third duration for holding a breath. In some embodiments, the method further includes the plurality of the user-related parameters further including: (6) a root of median squares of differences in successive RR intervals (RMSSD), (7) a power spectrum, (8) a total power, and (9) a deep breathing difference. In some embodiments, the heart rate sensor is resided in one of a mobile phone device associated with the user, a Bluetooth-enabled device, or a heart rate monitor associated with the user. In some embodiments, the heart rate sensor is resided in the at least one specialized programmed computing device. In some embodiments, the at least one specialized programmed computing device is the mobile phone device associated with the user. In some embodiments, the method includes instructing a subject to sufficiently use the method of claim 1, so as to result in a reduction of a blood sugar level of between 10-25%. In some embodiments, the subject is a diabetic patient.

In some embodiments, the instant invention provides for a computer system, including: at least one specialized computing device being specifically programmed with personalized wellbeing management software, where the personalized wellbeing management software is at least configured to: generate at least one personalized breathing instruction including at least: (i) a first indication identifying a first duration for inhaling, and (ii) a second indication identifying a second duration for exhaling; receive, in real time, by the at least one specialized programmed computing device, user sensor data from at least one heart rate sensor being associated with the user, determine, in real time, by the at least one specialized programmed computing device, user heart rate variability of the user (user HRV), based, at least in part, on the user sensor data, automatically calculate, by the at least one specialized programmed computing device, based on the user HRV, a parameter status percentage, based, at least in part, on a weighted sum of plurality of user-related parameters, including: (1) a first parameter identifying a Low frequency/High frequency ratio of the user, (2) a second parameter identifying a standard deviation of an instantaneous heart rate signal (SDNN) of the user, (3) a third parameter identifying a heart rate of the user, (4) a fourth parameter identifying a pnn50 of the user, and (5) a fifth parameter identifying a coherence of the user, so as to result in a calculated value of between 0.1-100%; provide to the user, in real time, by the at least one specialized programmed computing device, based on the parameter status percentage, at least one personalized breathing recommendation being configured to modify the parameter status percentage, where the at least one breathing recommendation includes: (i) a first breathing indication identifying a first adjustment a breathing rate of the user, (ii) a second breathing indication identifying a second adjustment to a breathing pattern of the user, (iii) or any combination thereof. In some embodiments, the system further includes a third indication identifying a third duration for holding a breath. In some embodiments, the system further includes the plurality of the user-related parameters further includes: (6) a root of median squares of differences in successive RR intervals (RMSSD), (7) a power spectrum, (8) a total power, or (9) a deep breathing difference. In some embodiments, the heart rate sensor is resided in one of a mobile phone device associated with the user, a Bluetooth-enabled device, or a heart rate monitor associated with the user. In some embodiments, the heart rate sensor is resided in the at least one specialized programmed computing device. In some embodiments, the at least one specialized programmed computing device is the mobile phone device associated with the user. In some embodiments, the personalized wellbeing management software is further configured to instruct a subject to sufficiently use the method of claim 9, so as to result in a reduction of a blood sugar level of between 10-25%. In some embodiments, the subject is a diabetic patient.

While a number of embodiments of the present invention have been described, it is understood that these embodiments are illustrative only, and not restrictive, and that many modifications may become apparent to those of ordinary skill in the art.

The invention claimed is:

1. A computer-implemented method, comprising:
   providing, to a user, in real time, by at least one specialized computing device being specifically programmed with wellbeing management software, at least one personalized breathing instruction via a graphical user interface displayed on the at least one specialized computing device, wherein the at least one personalized breathing instruction comprises at least:
   (i) a first indication identifying a first duration for inhaling, and
   (ii) a second indication identifying a second duration for exhaling;
   receiving, in real time, by the at least one specialized programmed computing device, user sensor data from at least one heart rate sensor being associated with the user, determining, in real time, by the at least one specialized programmed computing device, user heart rate variability of the user (user HRV), based, at least in part, on the user sensor data,
   automatically calculating, by the at least one specialized programmed computing device, stress level features comprising:
   (1) a Low frequency/High frequency ratio of the user,
   (2) a standard deviation of an instantaneous heart rate signal (SDNN) of the user,
   (3) a pnn50 of the user, and
   (4) a coherence of the user,
   linearizing, by the at least one specialized programmed computing device, each stress level feature and heart rate of the user to obtain a value from 0 to 100 for each respective feature;
   automatically calculating, by the at least one specialized programmed computing device, based on the user HRV, a parameter status percentage, based, at least in part, on a weighted sum of a plurality of user-related parameters, comprising:
   (1) a first parameter identifying a linearized Low frequency/High frequency ratio of the user,
   (2) a second parameter identifying a linearized SDNN of the user,
   (3) a third parameter identifying a linearized heart rate of the user,
   (4) a fourth parameter identifying a linearized pnn50 of the user, and
   (5) a fifth parameter identifying a linearized coherence of the user,
   providing, to the user, in real time, by the at least one specialized programmed computing device, based on the parameter status percentage, at least one personalized breathing recommendation being configured to modify the parameter status percentage,
   wherein the at least one breathing recommendation comprises:
   (i) a first breathing indication identifying a first adjustment to a breathing rate of the user,
   (ii) a second breathing indication identifying a second adjustment to a breathing pattern of the user,
   (iii) or any combination thereof.

2. The method of claim 1, further comprising a third indication identifying a third duration for holding a breath.

3. The method of claim 1, wherein the at least one heart rate sensor is resided in one of a mobile phone device associated with the user, a Bluetooth-enabled device, or a heart rate monitor associated with the user.

4. The method of claim 3, wherein the at least one heart rate sensor is resided in the at least one specialized programmed computing device.

5. The method of claim 3, wherein the at least one specialized programmed computing device is the mobile phone device associated with the user.

6. The method of claim 1, comprising:
   causing the at least one specialized programmed computing device to display one or more of Interactive Relaxation drills during a predefined time period based on the at least one breathing recommendation, so as to result in a reduction of a blood sugar level of between 10-25%.

7. The method of claim 6, wherein the user is a diabetic patient.

* * * * *